United States Patent
Fan et al.

(10) Patent No.: US 9,439,705 B2
(45) Date of Patent: Sep. 13, 2016

(54) INFLATABLE, STEERABLE BALLOON FOR ELEVATION OF TISSUE WITHIN A BODY

(71) Applicant: Smith & Nephew, Inc., Memphis, TN (US)

(72) Inventors: Wei Li Fan, Malden, MA (US); Marc Joseph Philippon, Edwards, CO (US); Paul Alexander Torrie, Marblehead, MA (US); David Leo Bombard, Edwards, CO (US)

(73) Assignee: Smith & Nephew, Inc., Memphis, TN (US)

(*) Notice: Subject to any disclaimer, the term of this patent is extended or adjusted under 35 U.S.C. 154(b) by 99 days.

(21) Appl. No.: 14/316,453

(22) Filed: Jun. 26, 2014

(65) Prior Publication Data

US 2014/0309646 A1    Oct. 16, 2014

Related U.S. Application Data

(62) Division of application No. 13/295,770, filed on Nov. 14, 2011, now Pat. No. 8,795,312.

(60) Provisional application No. 61/470,379, filed on Mar. 31, 2011, provisional application No. 61/426,892, filed on Dec. 23, 2010, provisional application No. 61/413,324, filed on Nov. 12, 2010.

(51) Int. Cl.
*A61B 17/02* (2006.01)
*A61B 17/88* (2006.01)
*A61B 17/00* (2006.01)

(52) U.S. Cl.
CPC ......... *A61B 17/8855* (2013.01); *A61B 17/025* (2013.01); *A61B 2017/00557* (2013.01); *A61B 2017/0275* (2013.01)

(58) Field of Classification Search
CPC .............. A61B 17/025; A61B 17/885; A61B 17/8852; A61B 17/8855; A61B 17/8858; A61B 2017/00557; A61B 2017/0256; A61B 2017/0268; A61B 2017/0275
See application file for complete search history.

(56) References Cited

U.S. PATENT DOCUMENTS 3,516,407 A    6/1970    Ruggero
4,545,390 A    10/1985   Leary
(Continued)

FOREIGN PATENT DOCUMENTS

WO    2007094374    8/2007

OTHER PUBLICATIONS

Examination Report for European Patent Application No. 11788722.4 dated Mar. 7, 2014, 6 pages.
(Continued)

*Primary Examiner* — Ryan J Severson
(74) *Attorney, Agent, or Firm* — Burns & Levinson LLP; Joseph M. Maraia

(57) ABSTRACT

An apparatus for elevating tissue within a body, including a tubular member having a proximal end and a distal end and a central axis defined therethrough, in which the tubular member comprises a first lumen and a second lumen, separately formed therein, a balloon secured to a region of the tubular member, in which a region of the tubular member is engagable with an injection mechanism, in which the engaged injection mechanism is engagable to be in communication with the first lumen of the tubular member, and in which the first lumen of the tubular member provides a path to an interior of the balloon.

16 Claims, 23 Drawing Sheets

(56) References Cited

U.S. PATENT DOCUMENTS

| | | | | |
|---|---|---|---|---|
| 4,927,412 | A | 5/1990 | Menasche | |
| 5,100,385 | A | 3/1992 | Bromander | |
| 5,188,630 | A | 2/1993 | Christoudias | |
| 5,190,046 | A | 3/1993 | Shturman | |
| 5,201,707 | A | 4/1993 | Kanai | |
| 5,224,933 | A | 7/1993 | Bromander | |
| 5,308,319 | A | 5/1994 | Ide et al. | |
| 5,324,260 | A | 6/1994 | O'Neill et al. | |
| 5,423,745 | A | 6/1995 | Todd et al. | |
| 5,649,909 | A | 7/1997 | Cornelius | |
| 5,797,877 | A | 8/1998 | Hamilton et al. | |
| 5,827,289 | A * | 10/1998 | Reiley | A61B 10/025 606/191 |
| 5,860,997 | A | 1/1999 | Bonutti | |
| 5,868,704 | A | 2/1999 | Campbell et al. | |
| 5,868,753 | A | 2/1999 | Schatz | |
| 5,980,485 | A | 11/1999 | Grantz et al. | |
| 6,066,154 | A * | 5/2000 | Reiley | A61B 17/7097 606/192 |
| 6,110,192 | A | 8/2000 | Ravenscroft et al. | |
| 6,221,080 | B1 | 4/2001 | Power | |
| 6,235,043 | B1 * | 5/2001 | Reiley | A61B 17/7097 604/101.01 |
| 6,248,110 | B1 * | 6/2001 | Reiley | A61B 10/025 606/192 |
| 6,641,587 | B2 * | 11/2003 | Scribner | A61B 17/1631 604/218 |
| 6,663,647 | B2 * | 12/2003 | Reiley | A61B 17/7097 604/96.01 |
| 6,716,216 | B1 * | 4/2004 | Boucher | A61B 17/1631 606/192 |
| 6,719,773 | B1 * | 4/2004 | Boucher | A61B 17/68 606/192 |
| 6,899,719 | B2 * | 5/2005 | Reiley | A61B 10/025 600/207 |
| 6,981,981 | B2 * | 1/2006 | Reiley | A61B 17/7097 128/898 |
| 7,014,633 | B2 * | 3/2006 | Cragg | A61B 17/1671 128/898 |
| 7,241,303 | B2 * | 7/2007 | Reiss | A61B 10/025 604/96.01 |
| 7,252,671 | B2 * | 8/2007 | Scribner | A61B 17/1631 606/86 R |
| 7,261,720 | B2 * | 8/2007 | Stevens | A61B 10/025 606/105 |
| 7,459,192 | B2 * | 12/2008 | Parsonage | A61M 25/104 428/35.7 |
| 7,488,337 | B2 * | 2/2009 | Saab | A61B 17/8855 604/96.01 |
| 7,524,329 | B2 * | 4/2009 | Rucker | A61F 2/88 606/192 |
| 7,547,317 | B2 * | 6/2009 | Cragg | A61B 17/1671 128/898 |
| 7,722,624 | B2 | 5/2010 | Boucher et al. | |
| 7,749,267 | B2 * | 7/2010 | Karmon | A61B 17/58 606/86 R |
| 7,781,038 | B2 | 8/2010 | Hamilton et al. | |
| 7,806,856 | B2 | 10/2010 | Bagaoisan et al. | |
| 7,811,290 | B2 * | 10/2010 | Rabiner | A61B 17/3472 606/94 |
| 7,815,649 | B2 * | 10/2010 | Layne | A61B 17/3417 606/105 |
| 7,875,035 | B2 * | 1/2011 | Boucher | A61B 17/68 606/105 |
| 7,938,835 | B2 * | 5/2011 | Boucher | A61B 17/1631 606/92 |
| 8,025,943 | B2 | 9/2011 | Hamilton et al. | |
| 8,092,480 | B2 * | 1/2012 | Layne | A61B 17/3417 606/192 |
| 8,177,744 | B2 * | 5/2012 | Saab | A61B 17/8855 604/103.08 |
| 8,216,182 | B2 * | 7/2012 | Saab | A61B 17/8855 604/103.08 |
| 8,226,657 | B2 * | 7/2012 | Linderman | A61B 17/8855 606/86 R |
| 8,277,506 | B2 * | 10/2012 | Krueger | A61B 17/14 606/279 |
| 8,348,956 | B2 * | 1/2013 | Rabiner | A61B 17/3472 606/94 |
| 8,394,056 | B2 * | 3/2013 | Saab | A61B 17/8855 604/103.08 |
| 8,454,646 | B2 * | 6/2013 | Saab | A61B 17/8855 604/96.01 |
| 8,454,647 | B2 * | 6/2013 | Saab | A61B 17/8855 604/96.01 |
| 8,454,663 | B2 * | 6/2013 | Boucher | A61B 17/1631 606/279 |
| 8,771,278 | B2 * | 7/2014 | Linderman | A61B 17/8855 606/279 |
| 8,795,312 | B2 * | 8/2014 | Fan | A61B 17/025 606/192 |
| 8,894,658 | B2 * | 11/2014 | Linderman | A61B 17/8805 606/86 R |
| 8,986,308 | B2 * | 3/2015 | Philippon | A61B 17/68 606/86 R |
| 9,095,393 | B2 * | 8/2015 | Schaus | A61B 17/8805 |
| 9,168,078 | B2 * | 10/2015 | Linderman | A61B 17/8805 |
| 2001/0011174 | A1 * | 8/2001 | Reiley | A61B 17/7097 606/86 R |
| 2001/0044626 | A1 * | 11/2001 | Reiley | A61B 17/7097 606/53 |
| 2001/0049531 | A1 * | 12/2001 | Reiley | A61B 10/025 606/93 |
| 2002/0013601 | A1 | 1/2002 | Nobles et al. | |
| 2002/0016583 | A1 * | 2/2002 | Cragg | A61B 17/1671 604/500 |
| 2002/0026195 | A1 * | 2/2002 | Layne | A61B 17/3417 606/92 |
| 2002/0032406 | A1 | 3/2002 | Kusleika | |
| 2002/0099384 | A1 * | 7/2002 | Scribner | A61B 17/1631 606/92 |
| 2002/0165571 | A1 | 11/2002 | Hebert et al. | |
| 2002/0177867 | A1 | 11/2002 | Hebert et al. | |
| 2002/0183778 | A1 * | 12/2002 | Reiley | A61B 17/7097 606/192 |
| 2003/0028211 | A1 | 2/2003 | Crocker et al. | |
| 2003/0032963 | A1 * | 2/2003 | Reiss | A61B 10/025 606/90 |
| 2003/0050644 | A1 * | 3/2003 | Boucher | A61B 17/3472 606/90 |
| 2003/0114878 | A1 | 6/2003 | Diederich et al. | |
| 2003/0130664 | A1 * | 7/2003 | Boucher | A61B 17/1631 606/86 R |
| 2003/0191489 | A1 * | 10/2003 | Reiley | A61B 17/7097 606/191 |
| 2003/0229372 | A1 * | 12/2003 | Reiley | A61B 17/7258 606/192 |
| 2004/0049203 | A1 * | 3/2004 | Scribner | A61B 17/1631 606/93 |
| 2004/0092948 | A1 * | 5/2004 | Stevens | A61B 10/025 606/96 |
| 2004/0097949 | A1 | 5/2004 | Bonutti | |
| 2004/0098017 | A1 * | 5/2004 | Saab | A61B 17/8855 606/192 |
| 2004/0153114 | A1 * | 8/2004 | Reiley | A61B 17/7097 606/192 |
| 2004/0153115 | A1 * | 8/2004 | Reiley | A61B 17/7097 606/192 |
| 2004/0167561 | A1 * | 8/2004 | Boucher | A61B 17/68 606/191 |
| 2004/0210231 | A1 * | 10/2004 | Boucher | A61B 17/1631 606/93 |
| 2004/0225296 | A1 * | 11/2004 | Reiss | A61B 10/025 606/90 |
| 2005/0090852 | A1 * | 4/2005 | Layne | A61B 17/3417 606/190 |
| 2005/0119662 | A1 * | 6/2005 | Reiley | A61B 10/025 606/92 |
| 2005/0124843 | A1 | 6/2005 | Singh | |
| 2005/0209595 | A1 * | 9/2005 | Karmon | A61B 17/58 606/76 |
| 2005/0261670 | A1 * | 11/2005 | Weber | A61L 29/126 606/21 |

(56) References Cited

U.S. PATENT DOCUMENTS

| | | | |
|---|---|---|---|
| 2005/0288678 A1* | 12/2005 | Reiley | A61B 17/8855 606/93 |
| 2006/0100635 A1* | 5/2006 | Reiley | A61B 17/8855 606/90 |
| 2006/0149136 A1 | 7/2006 | Seto et al. | |
| 2006/0229631 A1* | 10/2006 | Reiley | A61B 17/7097 606/93 |
| 2006/0235460 A1* | 10/2006 | Reiley | A61B 17/7258 606/192 |
| 2007/0010717 A1* | 1/2007 | Cragg | A61B 17/1671 600/300 |
| 2007/0010845 A1* | 1/2007 | Gong | A61B 17/8855 606/192 |
| 2007/0060941 A1* | 3/2007 | Reiley | A61B 10/025 606/192 |
| 2007/0093899 A1* | 4/2007 | Dutoit | A61B 17/686 623/17.11 |
| 2007/0255287 A1* | 11/2007 | Rabiner | A61B 17/3472 606/94 |
| 2007/0260178 A1 | 11/2007 | Skerven et al. | |
| 2007/0282346 A1* | 12/2007 | Scribner | A61B 17/1631 606/86 R |
| 2007/0299455 A1* | 12/2007 | Stevens | A61B 10/025 606/105 |
| 2007/0299460 A9* | 12/2007 | Boucher | A61B 17/68 606/191 |
| 2008/0051627 A1 | 2/2008 | Raju | |
| 2008/0051825 A1* | 2/2008 | Reiley | A61B 10/025 606/192 |
| 2008/0058823 A1* | 3/2008 | Reiley | A61B 10/025 606/92 |
| 2008/0058824 A1* | 3/2008 | Reiley | A61B 10/025 606/92 |
| 2008/0058828 A1* | 3/2008 | Reiley | A61B 10/025 606/94 |
| 2008/0058855 A1* | 3/2008 | Reiley | A61B 17/8855 606/192 |
| 2008/0058857 A1* | 3/2008 | Reiley | A61B 17/8855 606/198 |
| 2008/0058943 A1* | 3/2008 | Reiley | A61B 17/8855 623/17.16 |
| 2008/0065137 A1* | 3/2008 | Boucher | A61B 17/68 606/191 |
| 2008/0065138 A1* | 3/2008 | Reiley | A61B 17/8855 606/192 |
| 2008/0065142 A1* | 3/2008 | Reiley | A61B 17/8855 606/198 |
| 2008/0086073 A1 | 4/2008 | McDaniel | |
| 2008/0132934 A1* | 6/2008 | Reiley | A61B 17/8855 606/192 |
| 2008/0140083 A1* | 6/2008 | Reiley | A61B 17/8855 606/92 |
| 2008/0172081 A1* | 7/2008 | Reiss | A61B 10/025 606/192 |
| 2008/0221515 A1 | 9/2008 | Nagamatsu | |
| 2008/0269759 A1* | 10/2008 | Reiley | A61B 10/025 606/94 |
| 2008/0269795 A1* | 10/2008 | Reiley | A61B 10/025 606/192 |
| 2008/0269796 A1* | 10/2008 | Reiley | A61B 10/025 606/192 |
| 2008/0275392 A1 | 11/2008 | Nagamatsu | |
| 2009/0048623 A1 | 2/2009 | Lafosse et al. | |
| 2009/0076517 A1* | 3/2009 | Reiley | A61B 10/025 606/93 |
| 2009/0112210 A1* | 4/2009 | Philippon | A61B 17/68 606/62 |
| 2009/0112214 A1 | 4/2009 | Philippon et al. | |
| 2009/0177153 A1* | 7/2009 | Saab | A61B 17/8855 604/98.01 |
| 2009/0177200 A1* | 7/2009 | Saab | A61B 17/8855 606/63 |
| 2009/0177235 A1* | 7/2009 | Saab | A61B 17/8855 606/279 |
| 2009/0177236 A1* | 7/2009 | Saab | A61B 17/8855 606/279 |
| 2009/0240293 A1* | 9/2009 | Cragg | A61B 17/1671 606/86 R |
| 2009/0254033 A1 | 10/2009 | Suzuki et al. | |
| 2009/0281490 A1 | 11/2009 | McAuley et al. | |
| 2009/0312807 A1 | 12/2009 | Boudreault et al. | |
| 2010/0010303 A1 | 1/2010 | Bakos | |
| 2010/0010470 A1 | 1/2010 | Bates | |
| 2010/0082036 A1* | 4/2010 | Reiley | A61B 10/025 606/94 |
| 2010/0100114 A1 | 4/2010 | Berger | |
| 2010/0100184 A1* | 4/2010 | Krueger | A61B 17/14 623/17.12 |
| 2010/0168755 A1* | 7/2010 | Reiley | A61B 10/025 606/93 |
| 2010/0174235 A1 | 7/2010 | Yamaguchi | |
| 2010/0217086 A1 | 8/2010 | Deshmukh et al. | |
| 2011/0009871 A1* | 1/2011 | Rabiner | A61B 17/3472 606/94 |
| 2011/0112588 A1* | 5/2011 | Linderman | A61B 17/8855 606/86 R |
| 2011/0144688 A1* | 6/2011 | Reiss | A61B 10/025 606/192 |
| 2011/0196499 A1* | 8/2011 | Boucher | A61B 17/1631 623/17.16 |
| 2012/0053611 A1* | 3/2012 | Saab | A61B 17/8855 606/192 |
| 2012/0150210 A1 | 6/2012 | Fan et al. | |
| 2012/0239047 A1* | 9/2012 | Linderman | A61B 17/8805 606/93 |
| 2012/0277753 A1* | 11/2012 | Linderman | A61B 17/8855 606/92 |
| 2013/0197563 A1* | 8/2013 | Saab | A61M 29/02 606/191 |
| 2013/0204268 A1* | 8/2013 | Mafi | A61B 17/8855 606/105 |
| 2013/0218164 A1* | 8/2013 | Mueller | A61B 17/8819 606/93 |
| 2013/0289737 A1* | 10/2013 | Philippon | A61B 17/68 623/23.19 |
| 2014/0005711 A1* | 1/2014 | Saab | A61M 25/0144 606/191 |
| 2014/0046334 A1* | 2/2014 | Schaus | A61B 17/8805 606/93 |
| 2014/0222093 A1* | 8/2014 | Mafi | A61B 17/8855 606/86 R |
| 2014/0309646 A1* | 10/2014 | Fan | A61B 17/025 606/90 |
| 2015/0051604 A1* | 2/2015 | Linderman | A61B 17/8805 606/94 |
| 2015/0157372 A1* | 6/2015 | Philippon | A61B 17/68 623/22.12 |
| 2015/0257809 A1* | 9/2015 | Schaus | A61B 17/8805 606/93 |

OTHER PUBLICATIONS

International Report on Patentability and Written Opinion for PCT Application No. PCT/US2011/060613 dated May 14, 2013, 8 pages.
English Patent Abstract of WO 2007/094374 A1 from esp@cenet, published Aug. 23, 2007, 1 page.
International Search Reprt and Written Opinion for PCT Application No. PCT/US2011/060613 dated Mar. 20, 2012, 4 pages.
International Preliminary Report on Patentability for Patent Application No. PCT/US2011/060613 dated May 23, 2013, 9 pages.

* cited by examiner

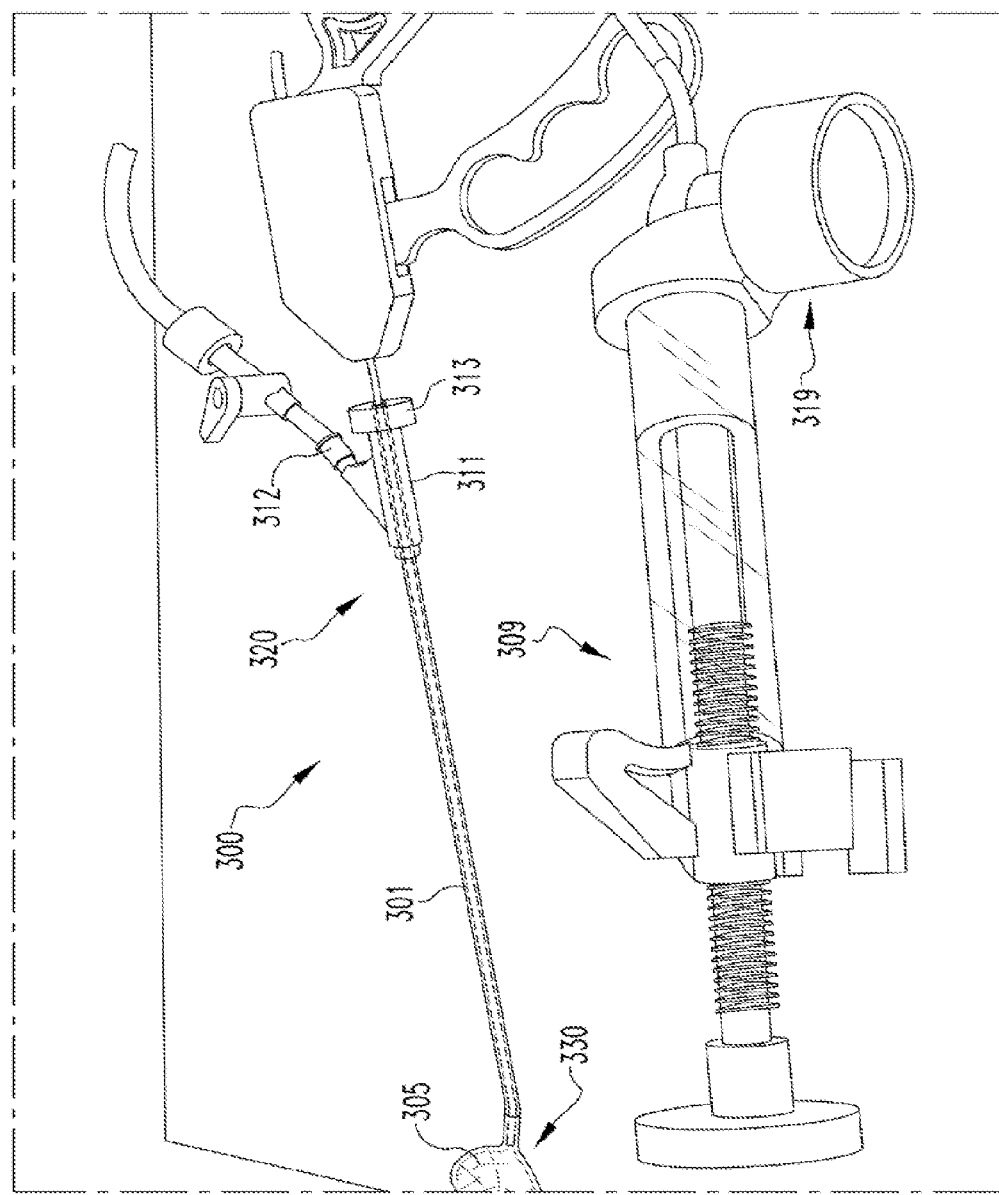

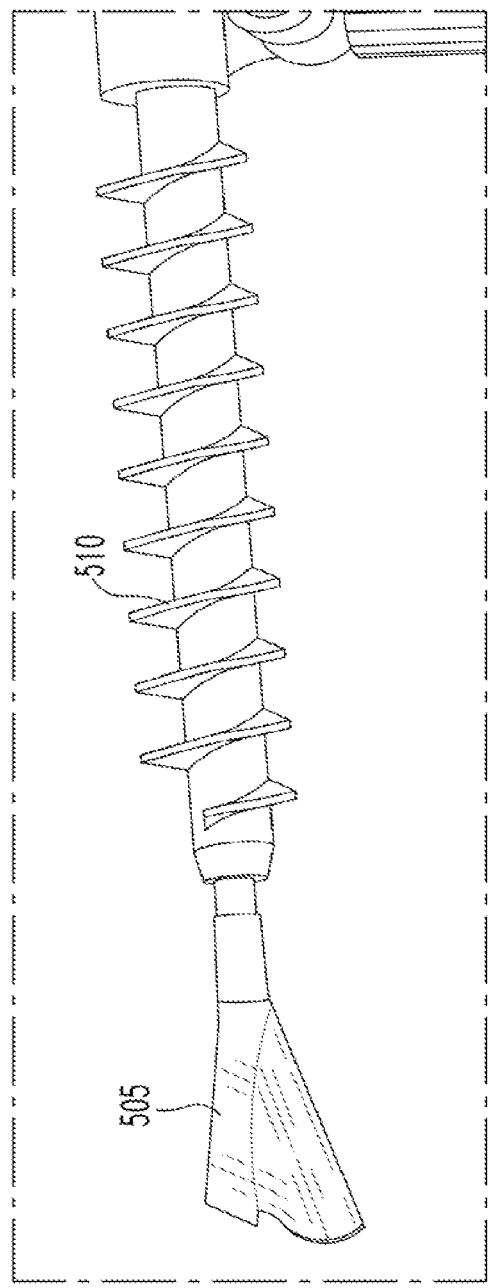

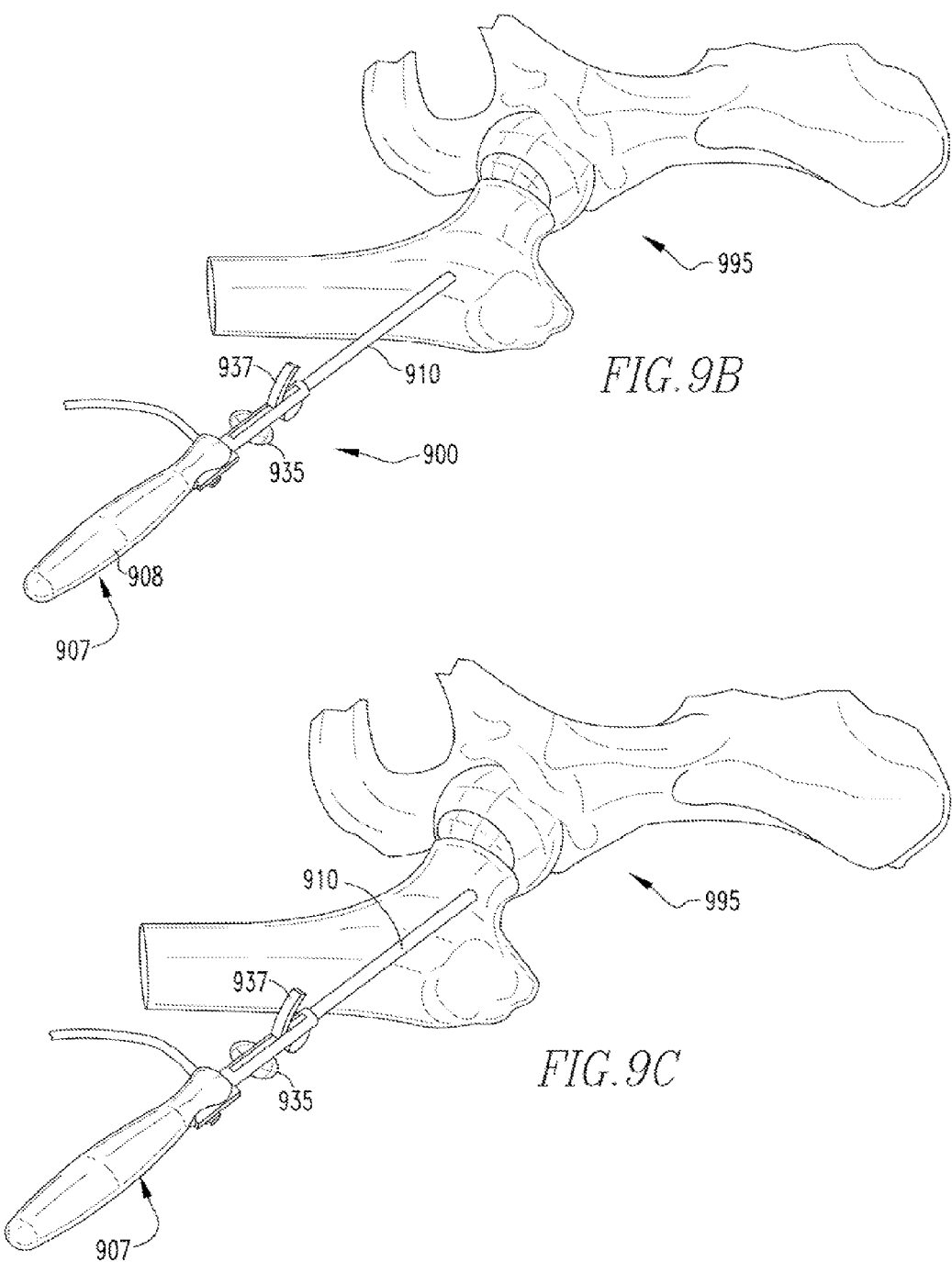

ically and medically in use are fluid operated retractors. Fluid operated retractors, such as an inflatable balloon or bladder, allow a surgeon to take potential spaces within the body and turn them into existing spaces safely, easily, and controllably in order to safely visualize appropriate tissue and operate. Such devices allow for selective retraction of tissue, either of hard tissue such as bone or soft tissue planes, to be moved out of the
INFLATABLE, STEERABLE BALLOON FOR ELEVATION OF TISSUE WITHIN A BODY

CROSS-REFERENCE TO RELATED APPLICATIONS

This application is a divisional of U.S. application Ser. No. 13/295,770, filed Nov. 14, 2011, which claims the benefit of U.S. Provisional Application Nos. 61/413,324, filed Nov. 12, 2010; 61/426,892, filed Dec. 23, 2010; and 61/470,379, filed Mar. 31, 2011, the entire contents of each of which are hereby incorporated herein by reference.

FIELD OF INVENTION

Embodiments disclosed herein relate generally to surgical devices. Specifically, embodiments disclosed herein relate to a surgical device for manipulating tissue within a patient's body.

BACKGROUND

Traditional surgical techniques may require a surgeon to make large incisions in a patient's body in order to access a tissue treatment region, or surgical site. In some instances, these large incisions may prolong the recovery time of and/or increase the scarring to the patient. As a result, minimally invasive surgical techniques are becoming more preferred among surgeons and patients because of the reduced size of the incisions required for various procedures. In some circumstances, for example, minimally invasive surgical techniques may reduce the possibility that the patient will suffer undesirable post-surgical conditions, such as scarring and/or infections. Further, such minimally invasive techniques can allow the patient to recover more rapidly as compared to traditional surgical procedures.

Generally, tissue distractors are used for expanding or separating tissues in order to create a space between the tissue to improve visualization and for increased working space during open surgery and minimally invasive surgery. Current methods used for increasing work space and improving visualization employ mechanical separators, such as metal retractors, scalpels, trocars, etc. Conventional metal retractors are often bulky and awkward and require substantially large open incisions in a skin surface which may damage large amounts of healthy tissue. Metal retractors often tear the muscle and tissue fibers apart, thereby increasing tissue trauma and healing time. Further, excess pressure from metal retractors may cause necrosis or tissue death, as it is difficult to monitor the pressure being applied to the body tissues. Other methods for separating tissue employ direct pressure of an unconfined flow of fluid such as water or saline during surgery. Problems with water pressurization include fluid extravasation including into and through the tissue itself. Further, increased pressure and swelling may result in the area, which may lead to edematous or swollen tissue. Excess water pressure may also lead to tissue damage or necrosis, as it difficult to monitor the pressure being applied to the body tissues.

Another class of devices commercially and medically in use are fluid operated retractors. Fluid operated retractors, such as an inflatable balloon or bladder, allow a surgeon to take potential spaces within the body and turn them into existing spaces safely, easily, and controllably in order to safely visualize appropriate tissue and operate. Such devices allow for selective retraction of tissue, either of hard tissue such as bone or soft tissue planes, to be moved out of the way to improve working space and visualization, which is of particular benefit while operating from within the body, e.g., minimally invasive surgery. These tissue retractors also permit working within the body without damaging a great deal of tissue in the path between a skin opening and the working area, by minimizing the external orifice or skin incision. Although such devices have achieved relative levels of success, improvements to such balloon tissue retraction devices would be advantageous. For example, during arthroscopic surgery, the joint areas of the body, such as the hip, knee, shoulder, and other joint areas, are approached via the use of an endoscope. Some joints are harder to access than others. For example, the hip joint differs from other joints in that a much thicker layer of soft tissue, known as the hip capsule, surrounds it. This thick layer makes changing the trajectory of instruments placed into the joint difficult and the importance of placing portals, or tissue passages, more critical than other joints.

Accordingly, there exists a need for a surgical device that may be modified to assist in cannula access to various treatment sites within a patient body for surgery.

SUMMARY OF INVENTION

According to one aspect of the present invention, there is provided an apparatus for elevating tissue within a body, comprising a tubular member having a proximal end and a distal end and a central axis defined therethrough, in which the tubular member comprises a first lumen and a second lumen, separately formed therein, a balloon secured to a first region of the tubular member, in which a second region of the tubular member is engagable with an injection mechanism, in which the engaged injection mechanism is engagable to be in communication with the first lumen of the tubular member, and in which the first lumen of the tubular member provides a path to an interior of the balloon.

According to another aspect of the present invention, there is provided a method for elevating tissue within a body, comprising providing a tubular member having a proximal end and a distal end and a central axis defined therethrough, in which a balloon secured to a first region of the tubular member, in which an injection mechanism is configured to inflate the balloon, in which a guide wire configured to engage with the tubular member, in which the guide wire is configured to manipulate the tubular member, inserting the distal end of the tubular member into a joint, in which the balloon is disposed, at least partially, within the joint, and inflating the balloon within the joint, causing a tissue to elevate relative to a position of the tissue prior to inserting the balloon into the joint.

According to yet another aspect of the present invention, there is provided a kit for elevating tissue within a body, comprising a tubular member having a proximal end and a distal end, a balloon configured to engage with the tubular member, an injection mechanism configured to engage with the tubular member, in which the injection mechanism is configured to inflate the balloon, and a guide wire configured to engage with the tubular member, in which the guide wire is configured to manipulate the tubular member.

BRIEF DESCRIPTION OF DRAWINGS

FIG. 3 is a perspective view of a balloon assembly engaged with an injection mechanism according to embodiments disclosed herein.

FIGS. 5A-5B are multiple views of a balloon assembly and a removable sheath according to embodiments disclosed herein.

FIGS. 9A-9C are multiple views of a balloon assembly with a sheath disposed about a hip joint according to embodiments disclosed herein.

DETAILED DESCRIPTION

In one aspect, embodiments disclosed herein relate to a maneuverable surgical device for manipulating tissue within a patient's body. Specifically, embodiments disclosed herein relate to a surgical device having a maneuverable balloon to manipulate tissue within a patient's body. Further, embodiments disclosed herein related to a dilator assembly having a balloon to dilate a tissue, a joint, and/or a hip capsule within a patient's body.

Embodiments of a surgical device having a steerable balloon disclosed herein may provide a maneuverable balloon assembly that may be maneuvered inside of a body. Additionally, the balloon assembly, according to embodiments disclosed herein, may allow for expanding or separating tissues in order to create a space between the tissue to improve visualization and for increased working space during open surgery and minimally invasive surgery. The balloon assembly, according to embodiments disclosed herein, may also allow a surgeon to maneuver into small, tight, potential spaces within the body and turn them into existing spaces safely, easily, and controllably in order to safely visualize appropriate tissue and operate.

Embodiments of a dilator assembly, according to embodiments disclosed herein, may pierce a tissue, a joint, and/or a hip capsule and dilate a circular hole in the tissue. The dilator assembly, according to embodiments disclosed herein, may allow a surgeon to avoid a sudden jolt when first breaking through hip capsule tissue with a cannula and obturator by dilating the tissue. Further, the dilator assembly, according to embodiments disclosed herein, may reduce dramatic scrapping of articular cartilage with a cannula.

Figure 1:
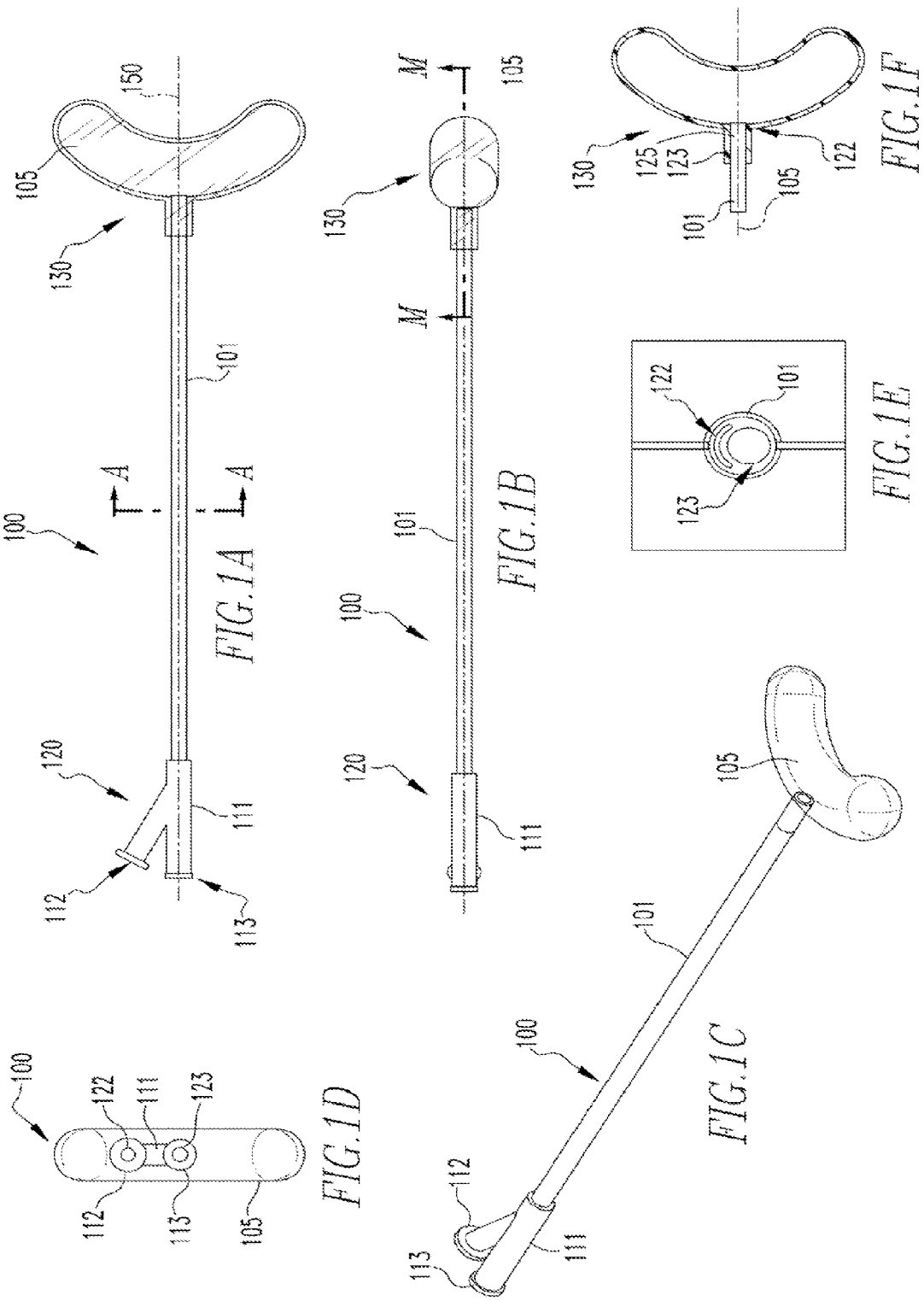
FIGS. 1A-1F are schematic drawings of multiple views of a balloon assembly in accordance with embodiments disclosed herein.

Referring, generally, to FIGS. 1A-1F, a balloon assembly 100 in accordance with embodiments disclosed herein is shown. The balloon assembly 100 is an apparatus for elevating tissue within a body and includes a tubular member 101. As shown, the tubular member 101 has a proximal end 120, a distal end 130, and a central axis 150 defined therethrough. As will be discussed below, in one or more embodiments, the tubular member 101 may include, at least, a first lumen 122 and a second lumen 123 separately formed therein. Although the tubular member 101 is shown having a first lumen 122 and a second lumen 123, those having ordinary skill in the art will appreciate that the tubular member may include more or less lumens formed therein than described above. For example, the tubular member may have one, three, four, or more lumens formed therein. Further, the tubular member 101 may be made of plastic or any material known in the art that may be deformed or deflected. Although the tubular member 101 shown in FIGS. 1A-1C is round, those having ordinary skill in the art will appreciate that the tubular member may be one of a variety of shapes and forms. For example, the tubular member may be square, triangular, hexagonal, or any other shape known in the art.

Referring to FIGS. 1A-1C, a balloon 105 may be secured to a region of the tubular member 101. As shown, the balloon 105 is secured to a region at or near the distal end 130 of the tubular member 101. The balloon 105 may be secured to the tubular member 101 by an adhesive or sealant known in the art. The balloon 105 can be made of medical grade plastic. In some embodiments, the balloon can be made of biodegradable material such as without limitation, polylactic acid materials, glycolides, and other materials that may polymerize and degrade with time in the body. Such materials can include biodegradable polymers including, but not limited to, glycolic acid-based polymers, such as polyglycolide (PGA); lactic acid-based polymers, such as polylactide (PLA); polyanhydrides; polyorthoesters; polyphosphazenes; poly(dioxanone) copolymers; poly(trimethylene carbonate) copolymers; poly(e-caprolactone) homopolymers and copolymers; LPLA; DLPLA; PCL; PDO; PGA-TMC; DLPLG; and polyhydroxybutyrate (PHB) and polyhydroxyvalerate (PHV) polymers and copolymers, such as Biopol(r) (Monsanto Co., St. Louis, Mo.). In other embodiments, the balloon 105 can be made of non-biodegradable material, for example, if the material is to remain intact for an extended period of time. The filling agent of the balloon 105 can be any medically safe material including fluids such as liquid saline, dextrose solutions, water, gases, such as air or nitrogen, and other fluids. Further, the fluid can be a hardenable material, known to those in the art. The balloon 105 can be provided in different sizes and shapes depending on the size of the tissue to be elevated. As shown, the balloon 105 is substantially kidney shaped and is configured to engage or fit on/around a femoral neck and elevate a tissue within a joint.

Further, an outer surface of the balloon 105 may be textured to provide increased friction between the balloon 105 and the area in contact with the balloon 105. Furthermore, the balloon 105 may become substantially rigid upon inflation, which may provide a reinforced support within a patient's body. Moreover, the term "balloon" is used broadly to encompass one or more balloons. For example, multiple balloons can be placed in position instead of one larger balloon as may be appropriate for the particular growth to be removed. Further, the balloon can include radio opaque material. As shown, the balloon is in an inflated state.

Further, as shown in FIGS. 1A-1C, a Y-adaptor 111 may be secured to a region of the tubular member 101. As shown, in one or more embodiments, the Y-adaptor 111 is secured to a region at or near the proximal end 120 of the tubular member 101. The Y-adaptor 111 may include an inflation port 112 and a guide wire port 113. The inflation port 112 of the Y-adaptor 111 may be engagable with an injection mechanism (not shown). The injection mechanism may be one of a syringe, a pump, and a plunger. However, those having ordinary skill in the art will appreciate that the injection mechanism may be any device or mechanism capable of injecting a fluid, i.e., a liquid or gas, known in the art.

In one or more embodiments, the injection mechanism may inject a fluid, e.g., a liquid or gas described above, through the inflation port 112 of the Y-adaptor 111, into the first lumen (not shown) formed through the tubular member 101, and into the balloon 105 to inflate the balloon 105. In one or more embodiments, the injection mechanism may also withdraw the fluid described above from the balloon 105, causing the balloon 105 to deflate. For example, this can be achieved by causing the injection mechanism to create a pull vacuum to withdraw the fluid from the balloon 105, back through the first lumen and the tubular member 101, and back into the injection mechanism.

In one or more embodiments, the injection mechanism may also include a pressure gauge (not shown) to monitor the pressure of the fluid that may be injected into the balloon 105. Further, in one or more embodiments, the injection mechanism, the Y-adaptor 111, and/or the tubular member 101 may include a seal (not shown). Once sealed, the seal may prevent a fluid, as described above, from withdrawing from the balloon 105, the first lumen, and/or the tubular member 101 back into the injection mechanism. The seal may be self-sealing, such as a check valve, a dome valve, and a self-sealing septum. The check valve can include valves such as read valves, flapper valves, and other self-sealing valves know in the art. In at least one embodiment, the seal can seal against the first lumen within the tubular member 101.

Referring still to FIGS. 1A-1C, the guide wire port 113 of the Y-adaptor 111 may be engagable with a guide wire (not shown). In one or more embodiments, the guide wire may be substantially disposed within the guide wire port 113 of the Y-adaptor 111 and substantially disposed within the second lumen (not shown) of the tubular member 101. The guide wire may be a device or mechanism that may be controllably manipulated, deformed, or deflected. For example, once substantially disposed within a tubular member, e.g., within the second lumen of the tubular member 101, the guide wire may controllably manipulate, deform, or deflect a tubular member, e.g., tubular member 101, between 1 degree and 100 degrees from the axis 150. Further, the balloon assembly 100 may be configured to rotate about the axis 150 when the tubular member is manipulated by the guide wire. Rotation about the axis 150 may increase maneuverability of the balloon assembly 100 within patient's body, as the balloon assembly 100 may be able to deflect/deform and rotate simultaneously. For example and without limitation, another exemplary guide wire device is shown in U.S. Pat. No. 6,283,960. The teaching of the above disclosure is incorporated herein by reference in its entirety.

In one or more embodiments, the guide wire may provide guidance for various tools, balloons, and other instruments inserted into a body. Further, variations on the use of the guide wire, including a guide wire external to balloon or internal to the balloon, no guide wire, guide wire at different steps, retracting the guide wire at different steps, and other variations are possible.

Alternatively, a substantially rigid, angled delivery rod (not shown) may be used in place of the guide wire. For example, the delivery rod may be a rigid, pre-bent, curved, or angled member configured to be received within the second lumen of the tubular member 101. Once the delivery rod is received within the second lumen of the tubular member 101, the delivery rod may cause the tubular member 101 to conform to the shape of the delivery rod and become angled. The deliver rod may rotate about the axis 150 and may allow for the tubular member 101 to be maneuvered within a body (not shown) without controllably manipulating, deforming, or deflecting the tubular member, as described with the guide wire above. A rotary slip (not shown) may also be disposed on the tubular member 101 and/or the delivery rod at a region at or near the distal end 130 of the tubular member 101 and may allow for tubular member 101 and/or the delivery rod to rotate about the axis 150 independently of the balloon 105. Such variations are contemplated and are intended to be included within the scope of the claims contained herein.

Referring to FIGS. 1A-1D, although the balloon assembly 100 is shown to include a Y-adaptor 111 secured at a region at or near the proximal end 120 of the tubular member 101, those having ordinary skill in the art will appreciate that a Y-adaptor 111 may not be necessary to achieve the function of the balloon assembly 100. For example, instead of a Y-adaptor, the proximal end of the tubular member, itself, may be formed to be substantially a Y-shape and configured to engage with an injection mechanism and a guide wire, such that a Y-adaptor would not be necessary to engage an injection mechanism and a guide wire to the tubular member.

Referring now to FIGS. 1A and 1D, a schematic drawing of the balloon assembly 100 and a back view of the balloon assembly 100 according to embodiments disclosed herein are shown, respectively. As shown, a first lumen 122 is formed in the inflation port 112 of the Y-adaptor 111. As will be shown below, the first lumen 122 may extend completely through the tubular member 101 and may provide a path to an interior of the balloon 105. In other words, the first lumen 122 may allow an injection mechanism (not shown) that is engaged with the inflation port 112 of the Y-adaptor 111 to be in communication with the tubular member and the balloon 105. For example, the injection mechanism may inject a fluid, e.g., a liquid or gas described above, into the first lumen 122, through the inflation port 112 of the Y-adaptor 111, through the tubular member, and into the balloon 105 to inflate the balloon 105. Further, as will be shown below, the second lumen 123 may not extend completely through the tubular member 101. However, the second lumen 123 may extend through the tubular member 101 such that a guide wire (not shown) disposed within the second lumen 123 may manipulate, deform, or deflect the tubular member 101. For example, the guide wire may be disposed through the guide wire port 113 of the Y-adaptor, disposed within the second lumen 123 and within the tubular member 101 such that a tip of the guide wire may be near a region at or near the distal end 130 of the tubular member 101. The Y-adaptor 111 may include a lock (not shown) on the inflation port 112 of the Y-adaptor 111 to secure the injection mechanism to the inflation port 112 of the Y-adaptor 111. Further, the Y-adaptor 111 may include a lock (not shown) on the guide wire port 113 of the Y-adaptor 111 to secure a portion of the guide wire to the guide wire port 113 of the Y-adaptor 111.

Referring to FIGS. 1A and 1E, a schematic drawing of the balloon assembly 100 and a cross-sectional view of the tubular member 101 of the balloon assembly 100 in accordance with embodiments disclosed herein are shown, respectively. As shown, the tubular member 101 includes a first lumen 122 and a second lumen 123 separately formed therethrough. Further, as shown, a cross-section of the first lumen 122 is substantially a crescent shape and a cross-section of the second lumen 123 is substantially circular in shape. Those having ordinary skill in the art will appreciate that the cross-sections of the first lumen 122 and the second lumen 123 are not limited to the shapes described above. For example, the cross-section of the first lumen may be any shape that may allow a fluid, e.g., a liquid or a gas described above, to move or travel through the first lumen. Further, the cross-section of the second lumen may be any shape that may allow a guide wire, as described above, to be disposed within the second lumen and manipulate, deform, or deflect the tubular member. For example, the cross-section of the second lumen may be any shape to substantially fit an outer diameter of the guide wire.

Referring to FIGS. 1A and 1F, a schematic drawing of the balloon assembly 100 and a cross sectional view of a region at or near the distal end of the tubular member 101 of the balloon assembly 100 in accordance with embodiments disclosed herein are shown, respectively. As shown, the first lumen 122 is connected to the balloon 105 and may allow a fluid, e.g., a liquid or gas described above, to move or travel through the tubular member 101 and into an interior of the balloon 105 to inflate the balloon 105. Further, as shown, the second lumen 123 is not formed completely through the tubular member 101. A distal stop 125 is formed on an end of the second lumen 123 at a region at or near the distal end 130 of the tubular member 101. As such, a guide wire (not shown) that is disposed within the second lumen 123 may abut the distal stop 125 of the second lumen 123, preventing the guide wire from penetrating into the interior of the balloon 105. The distal stop may be formed in a variety of manners, including manufacturing the tube so that the proximal end is open and the distal end is closed or locating a bead of glue or other substance within the lumen at the distal end of the lumen to block off the lumen. Other methods are also possible.

Further, although not shown, a removable sheath (not shown) may be disposed around a deflated balloon, i.e., balloon 105. The sheath may be made of a biodegradable polymer or a non-biodegradable material, as described above. For example, the sheath may be stainless steel, Teflon, or a type of plastic that can be removed. The sheath may be disposed around the deflated balloon and may assist with inserting the balloon assembly 100 into a body. For example, the sheath may provide a smooth insertion point for the balloon assembly 100 as the balloon assembly 100 is inserted into a body. Upon insertion, the sheath may be peeled away, retracted, or removed from around the balloon as the balloon is inflated.

Figure 2:
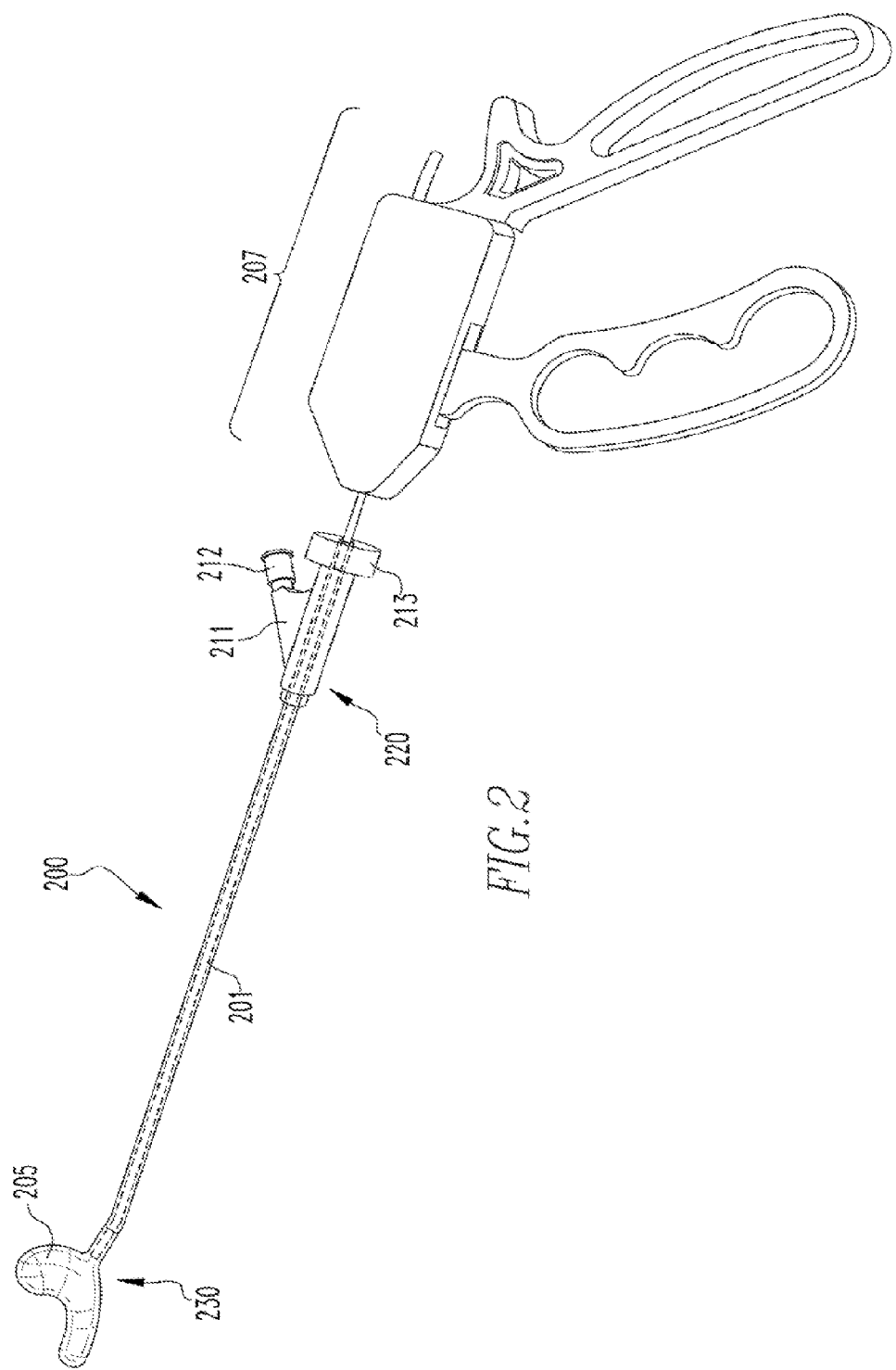
FIG. 2 is a perspective view of a balloon assembly in accordance with embodiments disclosed herein.

Referring now to FIG. 2, a perspective view of a balloon assembly 200 in accordance with embodiments disclosed herein is shown. As shown, the balloon assembly 200 includes a tubular member 201 having a balloon 205 secured to the tubular member 201 at a region at or near a distal end 230 of the tubular member 201. Further, as shown, the balloon assembly 200 includes a Y-adaptor 211 secured to the tubular member at a region at or near a proximal end 220 of the tubular member 201.

As shown, the Y-adaptor 211 includes an inflation port 212 and a guide wire port 213, in which a guide wire 207 is disposed within the guide wire port 213 and is engaged with the tubular member 201. As described above, the guide wire 207 may be disposed within a second lumen (not shown) that is formed in the tubular member 201 and may be controllably manipulated, deformed, or deflected to controllably manipulate, deform, or deflect the tubular member 201. Further, as described above, the inflation port 212 may be configured to engage with an injection mechanism (not shown). The injection mechanism may inject a fluid, e.g., a liquid or gas as described above, into the inflation port 212, through a first lumen (not shown) formed in the tubular member 201, through the tubular member 201, and into an interior of the balloon 205, inflating the balloon 205. As shown, the balloon 205 is in a deflated state.

Referring to FIG. 3, a perspective view of a balloon assembly 300 engaged with an injection mechanism 309 in accordance with embodiments disclosed herein is shown. As shown, the balloon assembly 300 includes a balloon 305 secured to a distal end 330 of a tubular member 301. Further, as shown, a Y-adaptor 311 is secured to a proximal end 320 of the tubular member 301 and includes an inflation port 312 and a guide wire port 313.

As shown, an injection mechanism 309 is engaged with the inflation port 312 of the Y-adaptor 311. Though not shown, the inflation port 312 of the Y-adaptor 311 is in communication with a first lumen (not shown), which is formed through the tubular member 301 from the inflation port 312 of the Y-adaptor 311 to the balloon 305. As such, a fluid, e.g., a liquid or gas described above, may be injected by the injection mechanism 309 into the inflation port 312 of the Y-adaptor, through the first lumen formed through the tubular member 301, and into an interior of the balloon 305, inflating the balloon 305. As discussed above, the injection mechanism 309, the Y-adaptor 311, and/or the tubular member 301 may include a seal. As shown, the injection mechanism 309 includes a pressure gage 319 that may be used to monitor the pressure of the fluid injected by the injection mechanism 309. Alternatively, in one or more embodiments, a pressure relief valve, or pressure relief tubing that may deform once a threshold pressure is reached, may be incorporated. In addition to monitoring the pressure of the fluid injected into the balloon 305, the pressure relief valve, or pressure relief tubing, may help alleviate excess pressure within the balloon 305 once the pressure within the balloon 305 exceeds a predetermined threshold.

Figure 4A:
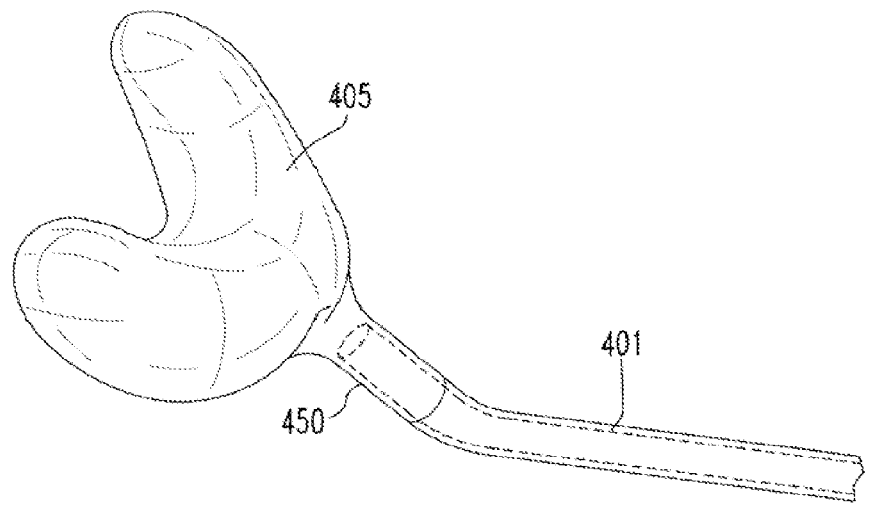
FIGS. 4A-4B are multiple views of a balloon assembly in a deflected position according to embodiments disclosed herein.
Figure 4B:
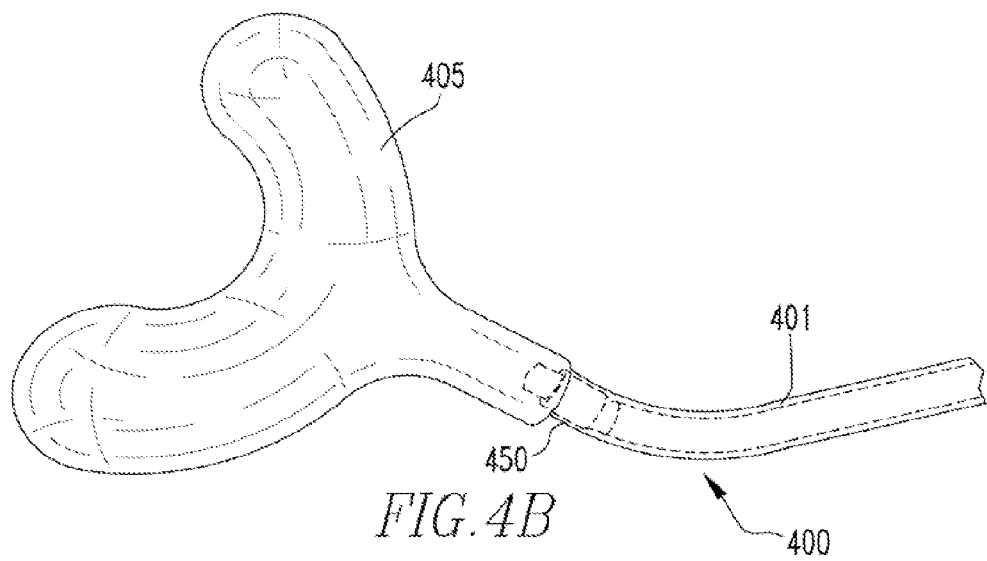

Referring to FIG. 4A-4B, multiple views of a balloon assembly 400 in a deflected position in accordance with embodiments disclosed herein are shown. As shown, a balloon 405 is secured to a tubular member 401, in which the tubular member 401 is deflected from a central axis 450 formed therethrough. Though not shown, in one or more embodiments, the tubular member 401 may be manipulated, deformed, or deflected by a guidewire (not shown) substantially disposed therein.

Figure 5A:
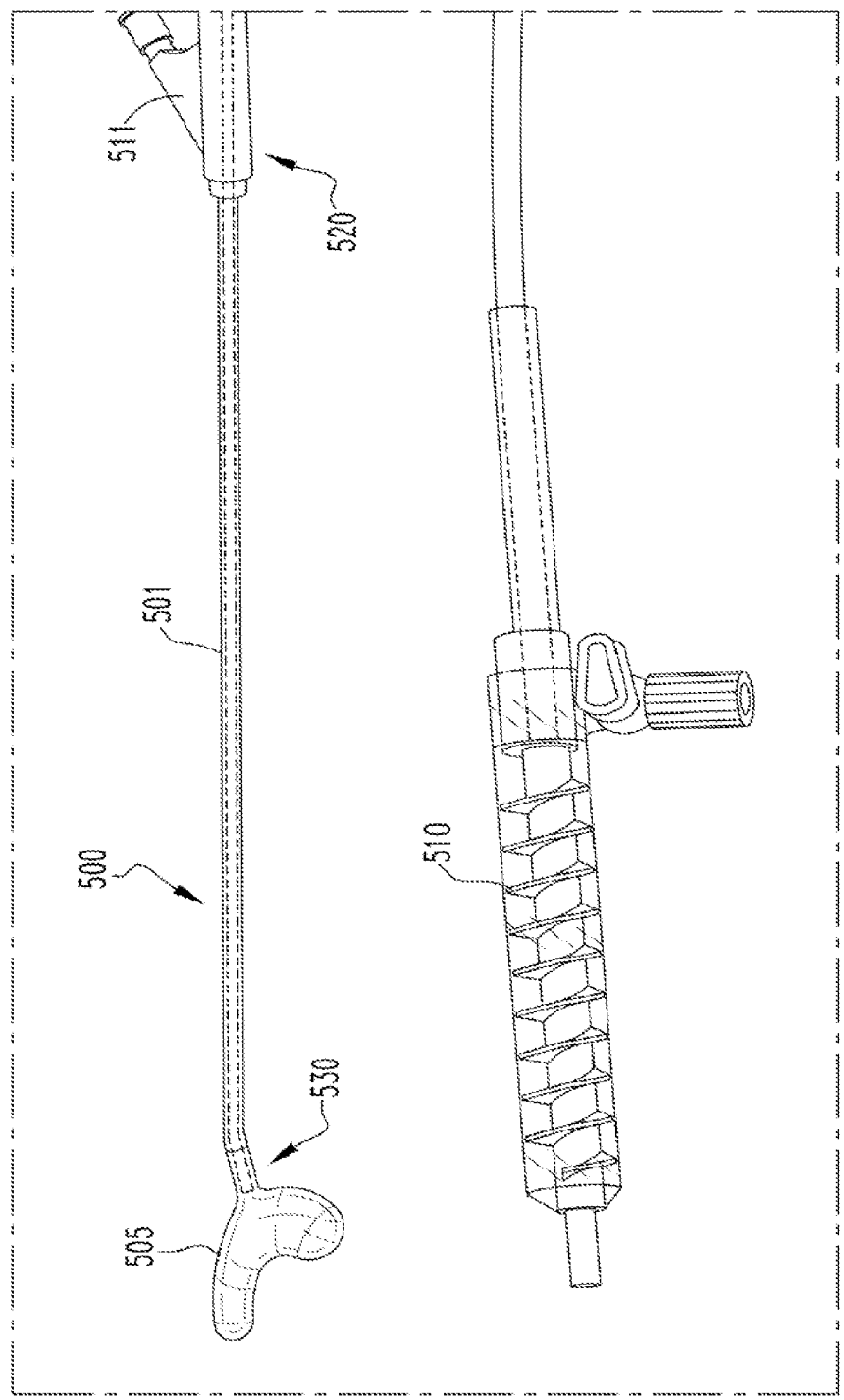

Referring now to FIG. 5A-5B, multiple views of a balloon assembly 500 and a removable sheath 510 in accordance with embodiments disclosed herein is shown. As shown in FIG. 5A, a balloon 505 is secured to a distal end 530 of a tubular member 501. Further, as shown in FIG. 5A, a Y-adaptor 511 secured to the tubular member at a region at or near a proximal end 520 of the tubular member 501. As shown in FIG. 5B, the removable sheath 510 is disposed over the tubular member 501 such that the balloon 505 is still visible. The sheath 510 may be disposed over the distal end 530 of the tubular member 501 and over the balloon 505. As such, the sheath 510 may provide a smooth insertion point for the balloon assembly 500 as the balloon assembly 500 is inserted into a body (not shown). Upon insertion, the sheath 510 may be peeled away, retracted, or removed from around the balloon 505 as the balloon 505 is inflated, as discussed above.

Figure 6:
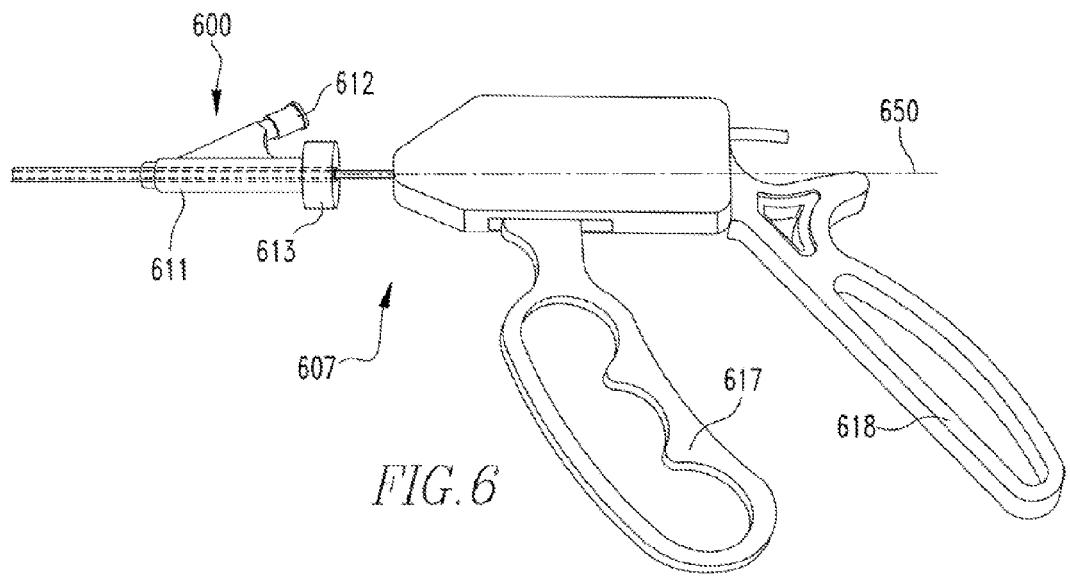
FIG. 6 is a side view of a balloon assembly engaged with a guide wire according to embodiments disclosed herein.

Referring to FIG. 6, a side view of a balloon assembly engaged with a guide wire 607 in accordance with embodiments disclosed herein is shown. As shown, a Y-adaptor 611 includes an inflation port 612 and a guide wire port 613. Further, as shown, the guide wire 607 is engaged with the guide wire port 613 of the Y-adaptor 611. In one or more embodiments, the guide wire 607 may include a handle 618 and a trigger 617. The guide wire 607 may be manipulated, deformed, or deflected by displacing the trigger 617 toward and away from the handle 618. Further, the Y-adaptor 611 may be able to rotate about a central axis 650 when the guide wire 607 is manipulated, deformed, or deflected.

Figure 7:
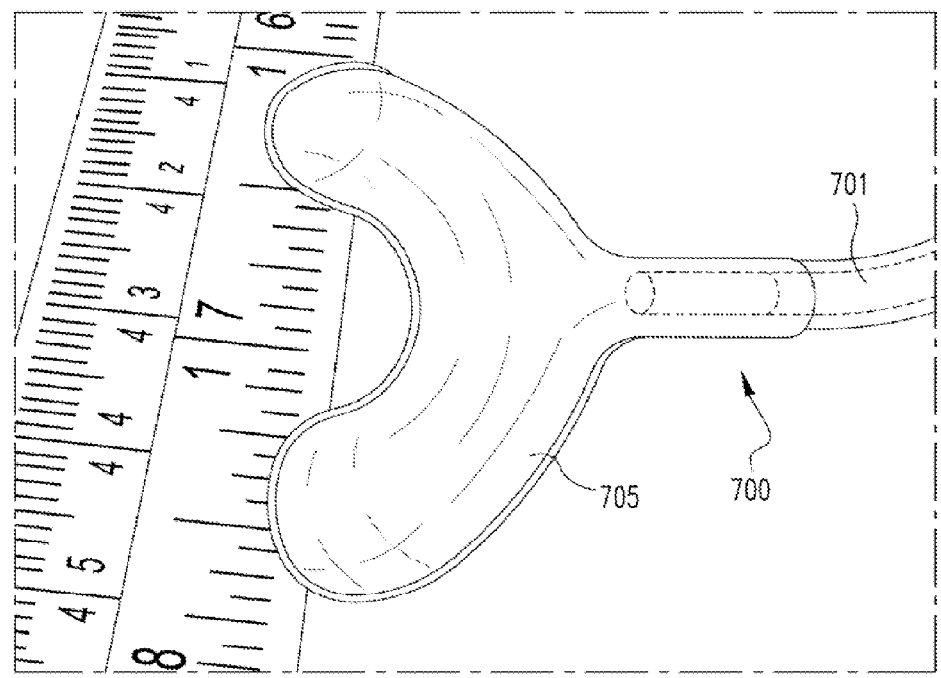
FIG. 7 is a close-up view of a balloon of a balloon assembly according to embodiments disclosed herein.

Referring to FIG. 7, a close-up view of a balloon 705 of a balloon assembly 700 in accordance with embodiments disclosed herein is shown. As shown, the balloon 705 may be substantially kidney shaped and may be roughly 4 cm in width. However, those having ordinary skill in the art will appreciate that the balloon 705 may be any shape, including round, square, oblong, and pyramidal, and is also not limited in size, as discussed above. Further, the balloon 705, according to one or more embodiments, may have an outer surface that is a textured surface. Furthermore, the balloon 705 may be formed and adapted to substantially engage with a femoral neck.

Figure 8:
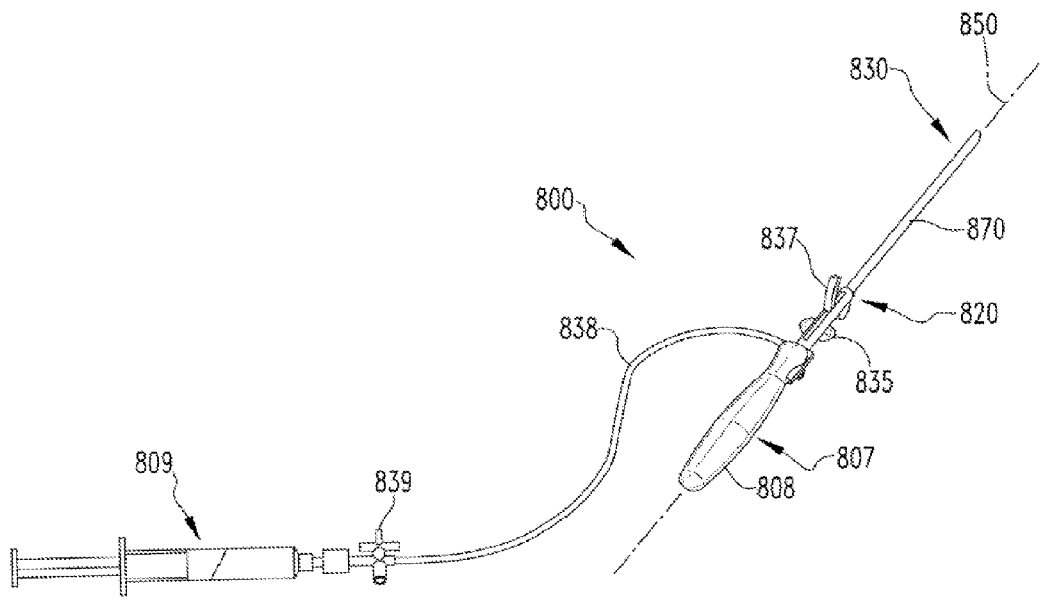
FIG. 8 is a perspective view of a balloon assembly with a sheath according to embodiments disclosed herein.

Referring to FIG. 8, a balloon assembly 800 with a sheath 810 in accordance with embodiments disclosed herein is shown. The balloon assembly 800 is an apparatus for elevating tissue within a body and includes a tubular member (not shown) and a central axis 850 formed therethrough. As shown, the balloon assembly 800 has a sheath 810 disposed around the tubular member and around a deflated balloon (not shown) that may be secured to a distal end of the tubular member. As the sheath 810 may be disposed around the tubular member and the deflated balloon, the sheath 810 may assist in the delivery of the balloon assembly 800 into a body (not shown). In one or more embodiments, a distal end 830 of the sheath 810 may be a beveled, or angled, end to assist in the delivery of the balloon assembly 800 into the body.

Further, as shown, a sheath trigger 837 may be disposed on a region near a proximal end 820 of the sheath 810. In one or more embodiments, the sheath trigger 837 may be used to move the sheath 810 in a direction that is parallel with the axis 850. Those having ordinary skill in the art will appreciate that the sheath trigger 837 may be any structure or feature that may assist with moving the sheath 810 in a direction that is parallel with the axis 850. For example, the sheath trigger 837 may be a protrusion, handle, or textured surface that may assist a user in moving the sheath 810 in a direction that is parallel with the axis 850. In one or more embodiments, the sheath trigger 837 may extend in a direction that is substantially perpendicular to the axis 850. Those having ordinary skill in the art will appreciate that a sheath trigger may not be required to move the sheath 810 in a direction that is parallel with the axis 850. For example, in one or more embodiments, the balloon assembly 800 may not include a sheath trigger, e.g., sheath trigger 837. As discussed above, the balloon assembly 800 may include a guide wire 807 that may be received within the tubular member such that the guide wire may manipulate, deform, or deflect the tubular member. As shown, the guide wire 807 may include a handle 808. The handle 808 of the guide wire 807 may provide a user with a gripping area to hold and operate the guide wire 807.

Further, as shown in FIG. 8, a sheath lock 835 may be disposed on a region near the proximal end 820 of the sheath around a region of the tubular member. In one or more embodiments, the sheath lock 835 may prevent the sheath 810 from moving toward the handle 808 of the guide wire 807 in a direction that is parallel to the axis 850. In one or more embodiments, the sheath lock 835 may be removable from the tubular member. In one or more embodiments, the sheath lock 835 may be coupled to the handle 808 of the guide wire 807.

Further, as shown, the balloon assembly 800 may include an injection mechanism 809. As shown, the injection mechanism 809 may include a stop valve 839 and may be connected to the tubular member by a tubing 838. Those having ordinary skill in the art will appreciate that the tubing 838 may be flexible or rigid, and may be made of any known material in the art. For example, the tubing 838 may be a flexible, rubber or plastic tubing. Alternatively, the tubing 838 may be made of a rigid plastic or other rigid material known in the art.

As discussed above, the injection mechanism 809 may be one of a syringe, a pump, a plunger, or any device or mechanism capable of injecting a fluid, i.e., a liquid or a gas, known in the art. In one or more embodiments, a fluid, e.g. a liquid or a gas described above, may be injected by the injection mechanism 809 into the tubular member and into an interior of the balloon, inflating the balloon. The stop valve 839 may be used to prevent backflow of fluid back into the injection mechanism 809 and may be used to assist in maintaining fluid pressure within the balloon. Those having ordinary skill in the art will appreciate that the stop valve 839 may be any valve, device, or mechanism that is capable of preventing fluid flow in a given direction. In one or more embodiments, the stop valve 839 may be automatically actuated. Alternatively, in one or more embodiments, the stop valve 839 may be manually actuated.

Figure 9A:
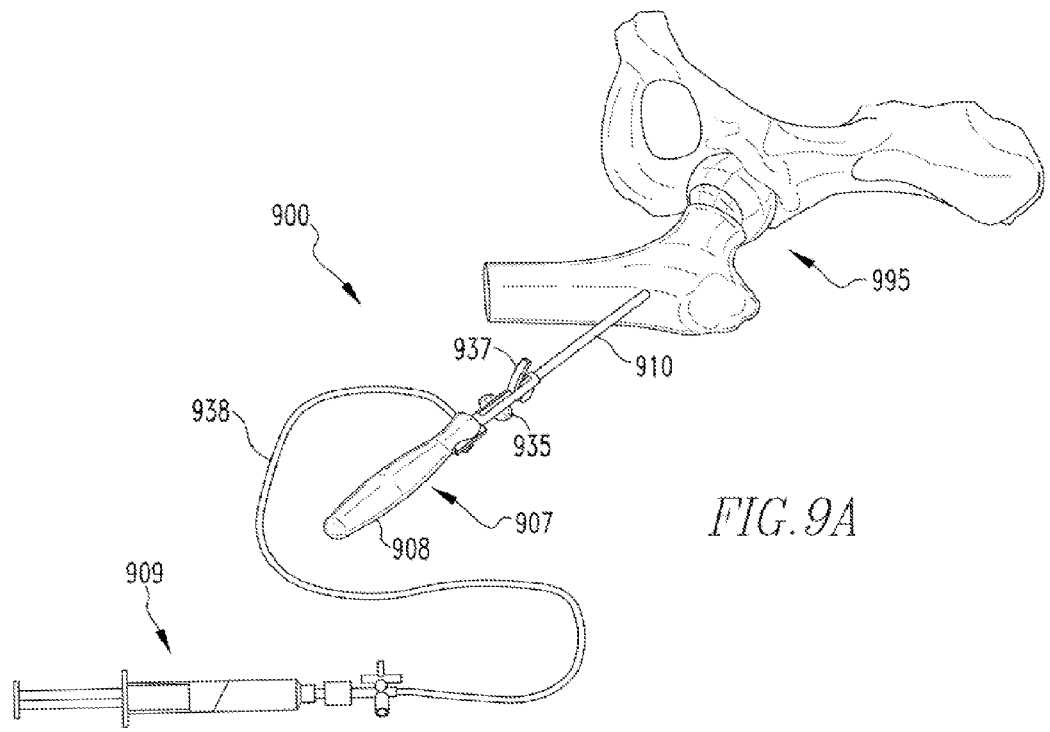

Referring, generally, to FIGS. 9A-9C, multiple views of a balloon assembly 900 with a sheath 910 disposed about a hip joint 995 in accordance with embodiments disclosed herein is shown. As shown in FIG. 9A, the balloon assembly 900 may include a tubular member (not shown), a balloon (not shown), a sheath 910, a sheath trigger 937, a sheath lock 935, a guide wire 907 having a handle 908, an injection mechanism 909, and a tubing 938 connecting the tubular member and the injection mechanism 909. As discussed above, the sheath 910 may be disposed around the tubular member and the deflated balloon, the sheath 910 may assist in the delivery of the balloon assembly 900 into the hip joint 995.

Figure 10A:
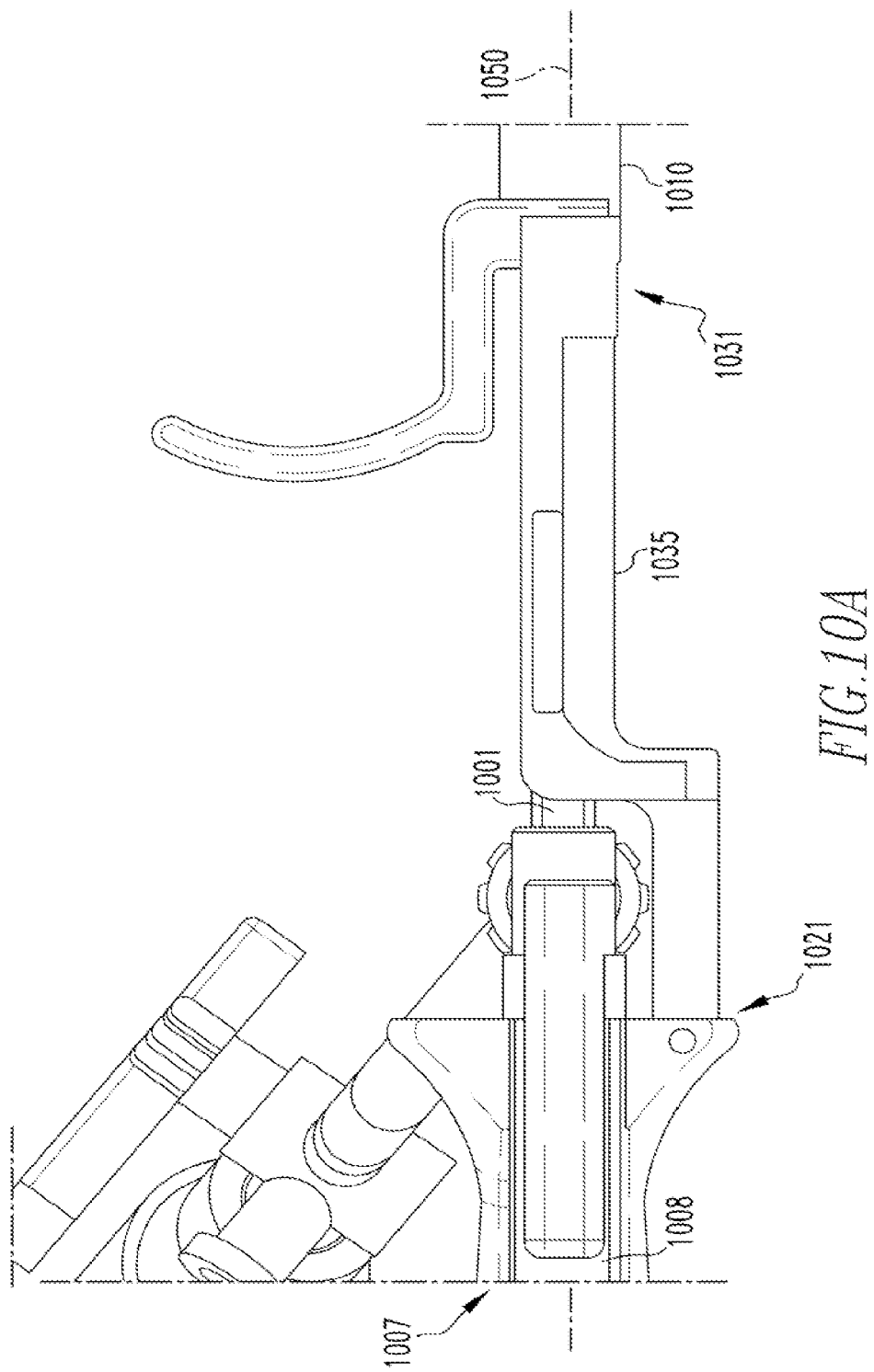
FIGS. 10A-10B are multiple views of a sheath lock in an engaged position according to embodiments disclosed herein.
Figure 10B:
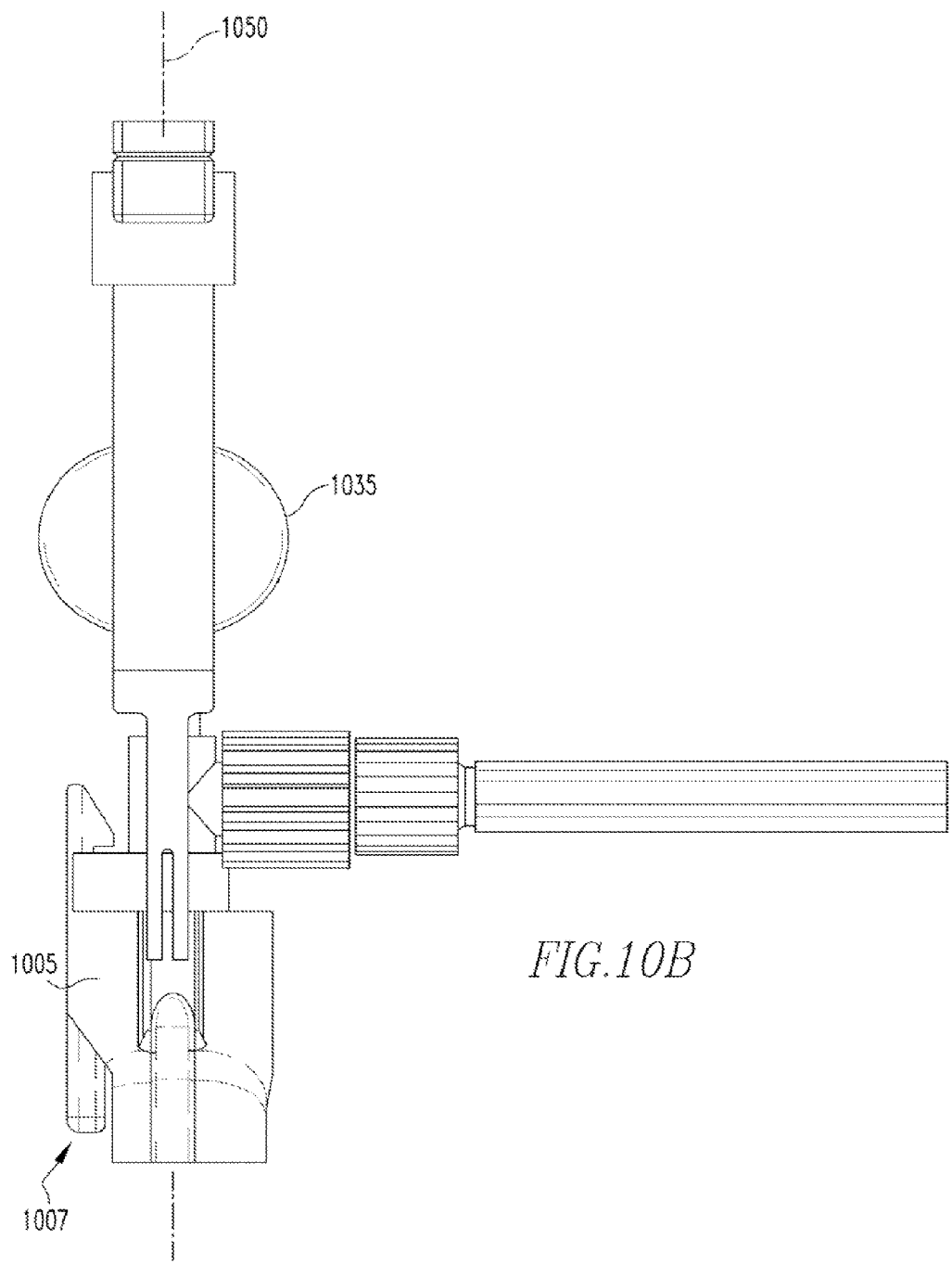
Figure 11A:
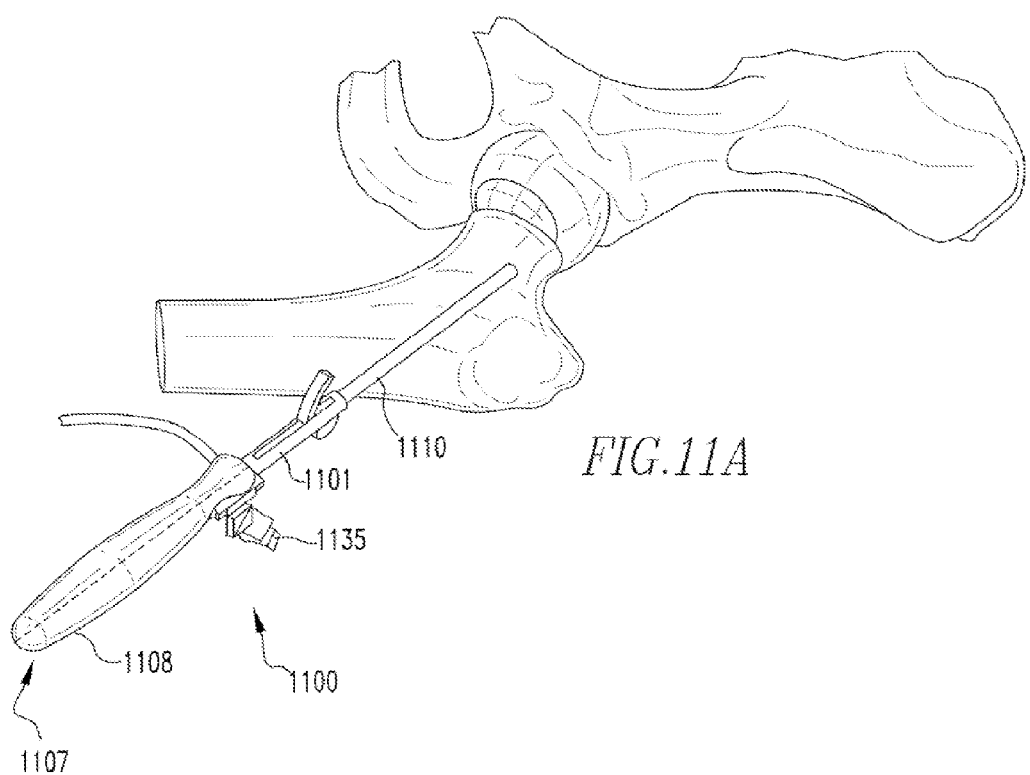
FIGS. 11A-11D are multiple views of a balloon assembly and a sheath lock in a disengaged position according to embodiments disclosed herein.
Figure 11B:
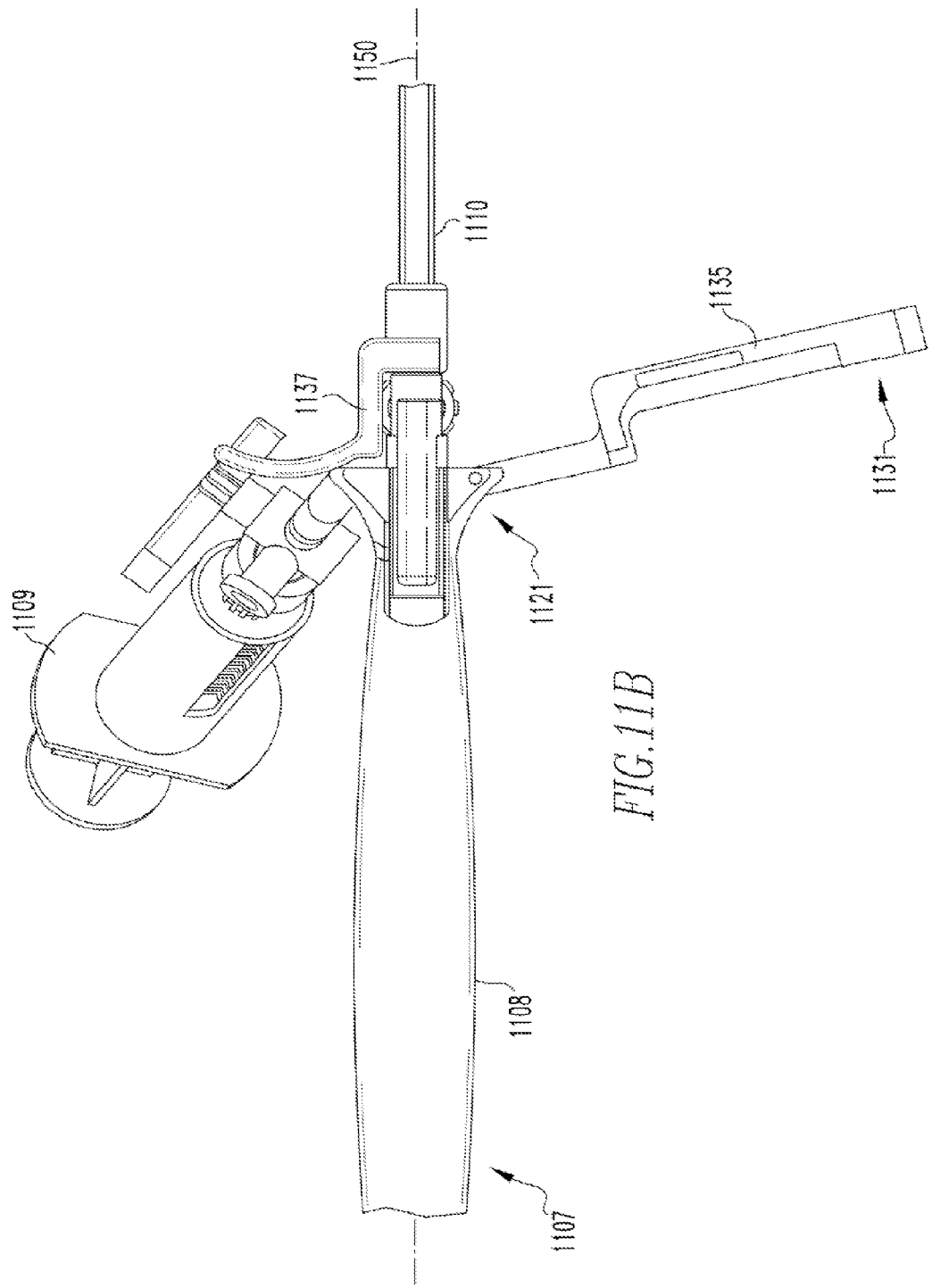
Figure 11C:
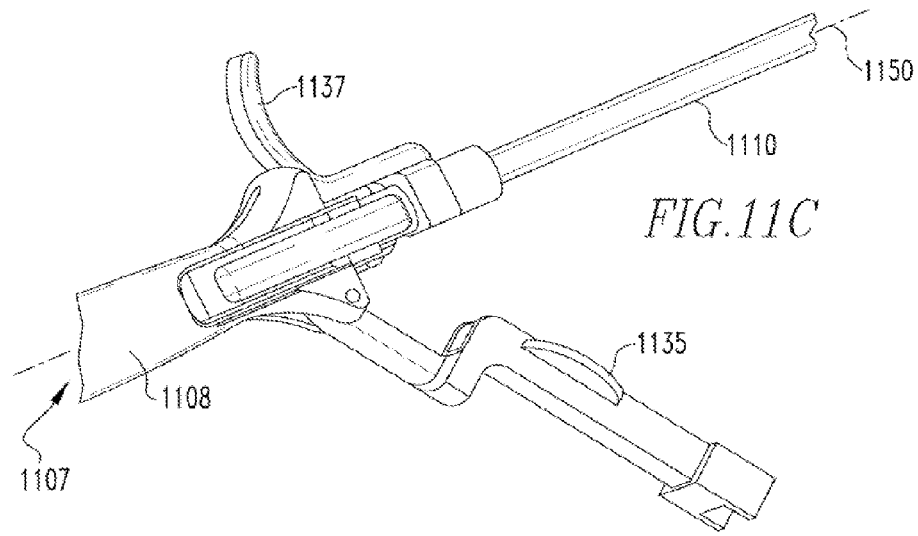
Figure 11D:
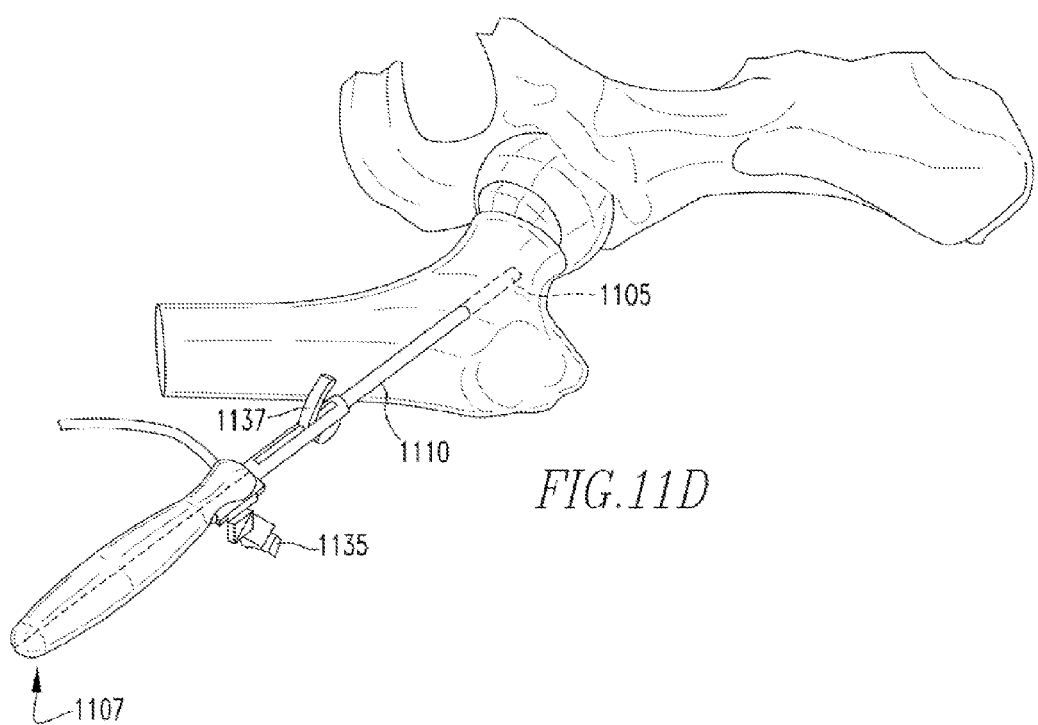

Referring, generally, to FIGS. 10A and 10B, a side view and a bottom view of a sheath lock 1035 in an engaged position in accordance with embodiments disclosed herein are shown, respectively. As shown, the sheath lock 1035 may be engaged with a tubular member 1001. In the engaged position, the sheath lock 1035 may be disposed around a region of the tubular member 1001. As shown, the sheath lock 1035 may include a first end 1021 and a second end 1031. In one or more embodiments, the first end 1021 of the sheath lock 1035 may be coupled to a handle 1008 of a guide wire 1007, in which the sheath lock 1035 may pivot about the first end 1021 of the sheath lock 1035 on the handle 1008 of the guide wire 1007. Those having ordinary skill in the art will appreciate that the sheath lock 1035 may not be coupled to the handle 1008 of the guide wire 1007. For example, in one or more embodiments, the sheath lock 1035 may be configured to engage with the tubular member 1001 and may not be coupled to the handle 1008 of the guide wire 1007. In the engaged position, the sheath lock 1035 may prevent a sheath 1010 from moving toward the handle 1008 of the guide wire 1007 in a direction parallel to a central axis 1050.

Referring, generally, to FIGS. 11A-11D, multiple views of a balloon assembly 1100 and a sheath lock 1135 in a disengaged position in accordance with embodiments disclosed herein are shown. As shown, the sheath lock 1135 may be disengaged from a tubular member 1101. In the disengaged position, the sheath lock 1135 may not be disposed around a region of the tubular member 1101. As shown, the sheath lock 1135 may include a first end 1121 and a second end 1131.

As discussed above, in one or more embodiments, the first end 1121 of the sheath lock 1135 may be coupled to a handle 1108 of a guide wire 1107, in which the sheath lock 1135 may pivot about the first end 1121 of the sheath lock 1135 on the handle 1108 of the guide wire 1107. In the disengaged position, the sheath 1110 may move toward the handle 1108 of the guide wire 1107 in a direction parallel to a central axis 1150. In one or more embodiments, the sheath trigger 1137 may be used to move the sheath 1110 in a direction that is parallel with the axis 1150. For example, in one or more embodiments, the sheath trigger 1137 may be used to move the sheath 1110 toward the handle 1108 of the guide wire 1107 in a direction parallel to a central axis 1150. Those having ordinary skill in the art will appreciate that a sheath trigger may not be required to move the sheath 1110 in a direction that is parallel with the axis 1150. For example, in one or more embodiments, the balloon assembly 1100 may not include a sheath trigger, e.g., sheath trigger 1137.

In one or more embodiments, moving the sheath 1110 toward the handle 1108 of the guide wire 1107 in a direction parallel to a central axis 1150 may expose, e.g., deploy, a balloon (not shown) that may be secured to a region near a proximal end of the tubular member 1101. In one or more embodiments, the sheath 1110 may be moved toward the handle 1108 of the guide wire 1107 in a direction parallel to a central axis 1150 such that the sheath trigger 1137 may abut the handle 1108 of the guide wire 1107 to expose the balloon. Once the balloon is exposed from the sheath 1110, the balloon may be able to be inflated, as discussed above.

Figure 12A:
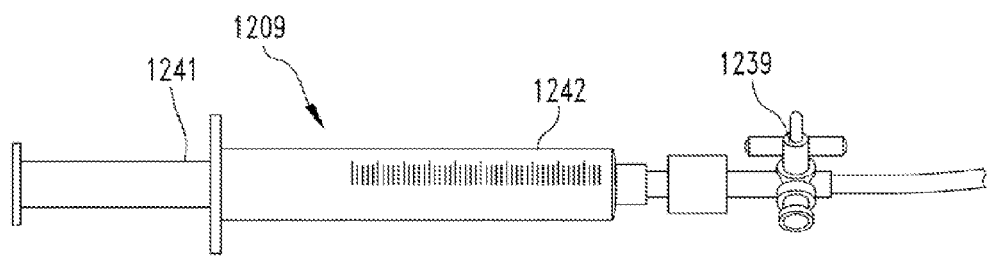
FIGS. 12A-12C are multiple views of an injection mechanism and a valve according to embodiments disclosed herein.
Figure 12B:
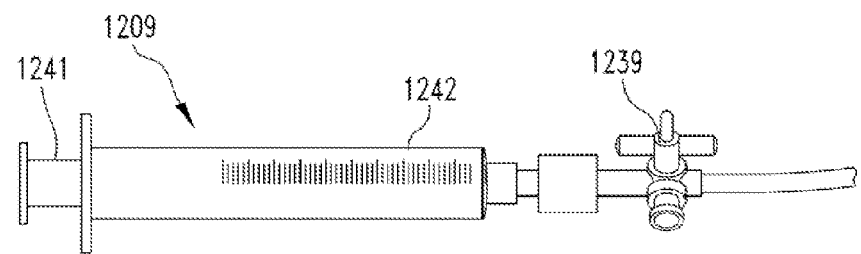
Figure 12C:
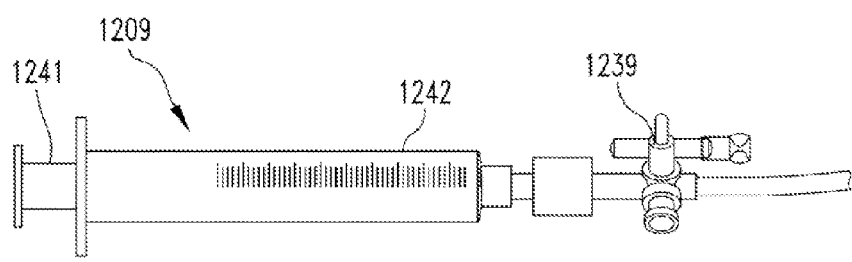

Referring to FIGS. 12A-12C, multiple views of an injection mechanism 1209 and a stop valve 1239 in accordance with embodiments disclosed herein are shown. As shown, the injection mechanism may be a syringe having a plunger 1241 and a barrel 1242. As shown in FIG. 12A, the plunger 1241 may be at least partially disposed within the barrel 1242 of the injection mechanism 1209. In one or more embodiments, the barrel 1242 of the injection mechanism 1209 may be filled with any medically safe material, including fluids such as liquid saline, dextrose solutions, water, gases, such as air or nitrogen, and other fluids. Further, the fluid can be a hardenable material, known to those in the art.

As shown in FIG. 12A, the stop valve 1239 may be in an open position and may allow fluid to move from the injection mechanism, through the stop valve 1239. As shown in FIG. 12B, the plunger 1241 may be fully disposed within the barrel 1242 of the injection mechanism 1209 such that any fluid within the barrel 1242 of the injection mechanism 1209 may be moved out of the injection mechanism, through the stop valve 1239. Further, as shown in FIG. 12A, the stop valve 1239 may be in an open position and may allow fluid to move from the injection mechanism, through the stop valve 1239. In one or more embodiments, by fully disposing the plunger 1241 within the barrel 1242 of the injection mechanism 1209, a balloon (not shown) may be inflated. As shown in FIG. 12C, the plunger 1241 may be fully disposed within the barrel 1242 of the injection mechanism 1209 such that any fluid within the barrel 1242 of the injection mechanism 1209 may be moved out of the injection mechanism, through the stop valve 1239. Further, the stop valve 1239 may be in a closed position and may prevent backflow of fluid back into the injection mechanism 1209 and may be used to assist in maintaining fluid pressure within the balloon. Those having ordinary skill in the art will appreciate that the stop valve 1239 may be any valve, device, or mechanism that is capable of preventing fluid flow in a given direction.

Figure 13:
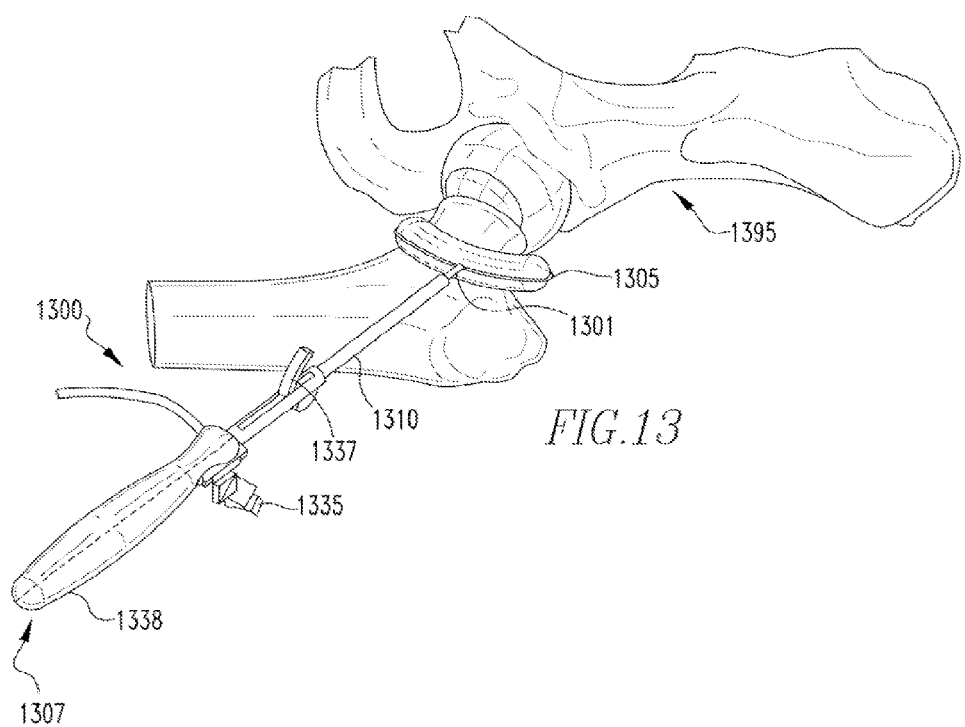
FIG. 13 is a perspective view of a balloon assembly in an inflated position according to embodiments disclosed herein.

Referring to FIG. 13, a perspective view of a balloon assembly 1300 in an inflated position in accordance with embodiments disclosed herein is shown. As shown, the balloon assembly 1300 may include a tubular member 1301, a balloon 1305, a sheath 1310, a sheath trigger 1337, a sheath lock 1335, and a guide wire 1307 having a handle 1308.

As shown, the sheath lock 1335 may be disengaged from a tubular member 1301. In the disengaged position, the sheath lock 1335 may not be disposed around a region of the tubular member 1301 and may allow the sheath 1310 to move toward the handle 1308 of the guide wire 1307. As shown, the sheath trigger 1337 may abut the handle 1308 of the guide wire 1107 and expose the balloon 1305 from the sheath 1310. Those having ordinary skill in the art will appreciate that the sheath trigger 1337 may not necessarily need to abut the handle 1308 of the guide wire 1307 to expose the balloon 1305 from the sheath 1310. For example, the balloon 1305 may be exposed from the sheath 1310 without the sheath trigger 1337 abutting the handle 1308 of the guide wire 1307. Further, as shown, the balloon 1305 is inflated, i.e., filled with a fluid discussed above. As discussed above, the balloon 1305 may be substantially kidney shaped and may be configured to engage a femoral neck and elevate a tissue within a hip joint 1395.

Figure 14A:
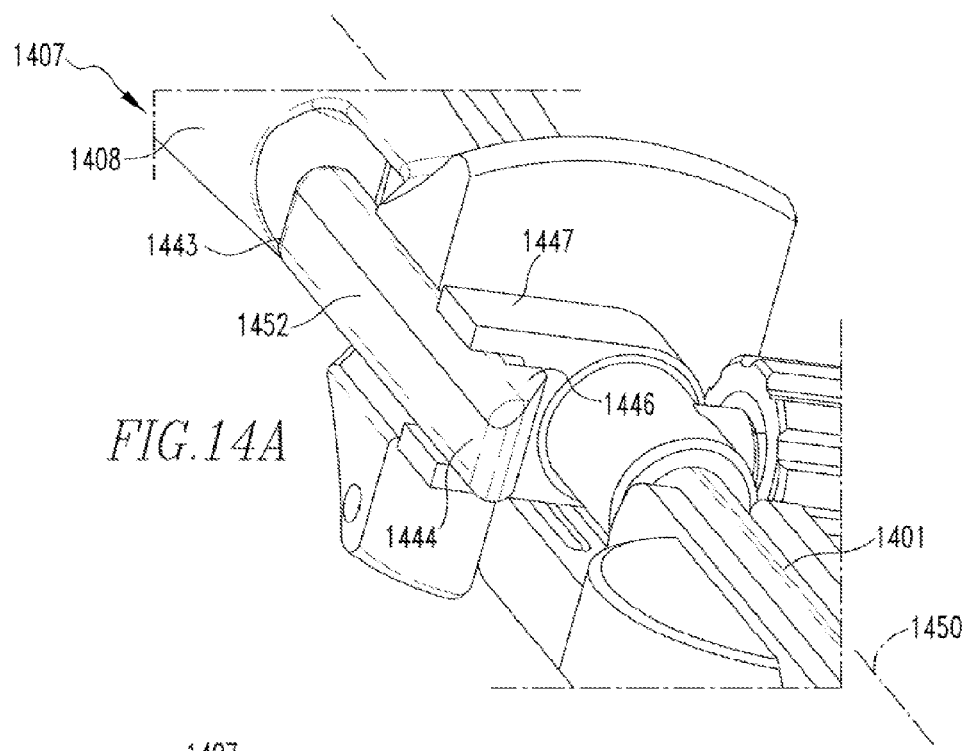
FIG. 14A-14B are multiple views of an engagement latch of a handle of a guide wire in an engaged position according to embodiments disclosed herein.
Figure 14B:
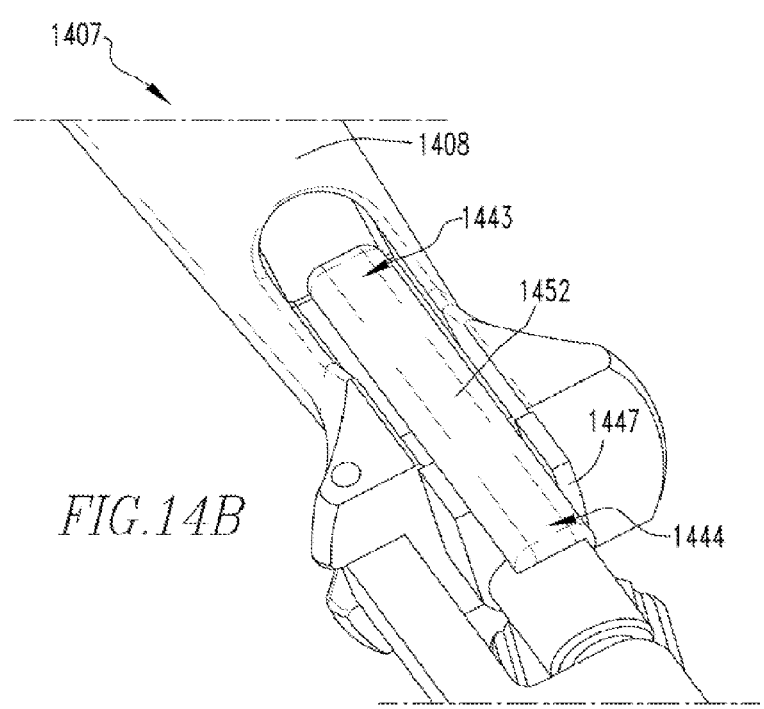

Referring, generally, to FIGS. 14A and 14B, multiple views of an engagement latch 1452 of a handle 1408 of a guide wire 1407 in an engaged position in accordance with embodiments disclosed herein are shown. As shown, the engagement latch 1452 may be coupled to the handle 1408 of the guide wire 1407 and may include a first end 1443, a second end 1444, and a detent 1446 extending from a region near the second end 1444 of the engagement latch 1452.

In one or more embodiments, the detent 1446 of the engagement latch 1452 may prevent the handle 1408 of the guide wire 1407 from moving away from the tubular member 1401 in a direction that is parallel to a central axis 1450. In other words, the detent 1446 of the engagement latch 1452 may prevent the guide wire 1407 from being withdrawn from the tubular member 1401. In one or more embodiments, the engagement latch 1452 may be configured to engage with an engagement member 1447 of a tubular member 1401. In one or more embodiments, the engagement member 1447 of the tubular member 1401 may be disposed on a region near a proximal end of the tubular member 1401.

As shown, the engagement latch 1452 of the handle 1408 of the guide wire 1407 is engaged with the engagement member 1447 of the tubular member. In one or more embodiments, the engagement latch 1452 of the handle 1408 of the guide wire 1407 may be a see-saw-type mechanism, such that moving the first end 1443 of the engagement latch 1452 in a first direction may cause the second end 1444 of the engagement latch 1452 to move in a second direction that is opposite to the first direction. For example, in one or more embodiments, by pressing on the first end 1443 of the engagement latch 1452, the second end 1444 of the engagement latch may disengage from the engagement member 1447 of the tubular member 1401. In one or more embodiments, the engagement latch 1452 and the detent 1446 of the engagement latch 1452 may no longer in contact with the engagement member 1447 in the disengaged position. As such, in one or more embodiments, the guide wire 1407 may be withdrawn from the tubular member 1401 with the engagement latch 1452 in the disengaged position.

Figure 15:
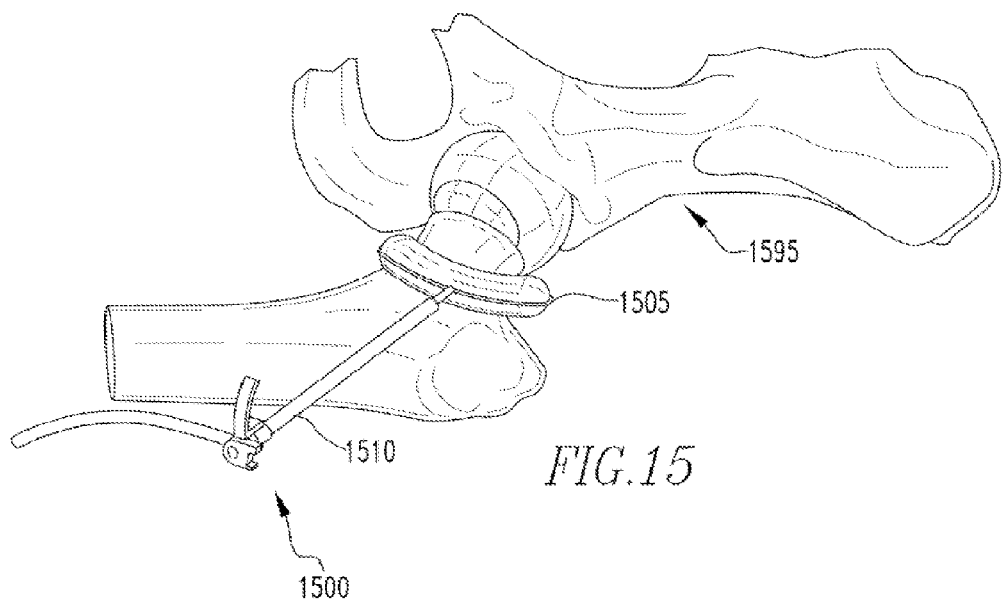
FIG. 15 is a perspective view of a balloon assembly in an inflated position, in which a guide wire is disengaged and removed from the balloon assembly according to embodiments disclosed herein.

Referring to FIG. 15, a perspective view of a balloon assembly 1500 in an inflated position in a hip joint 1595, in which a guide wire (not shown) is disengaged and removed from, e.g., withdrawn from, the balloon assembly 1500 in accordance with embodiments disclosed herein is shown. As shown, the sheath 1510 is positioned to expose the balloon 1505, and the balloon 1505 is inflated, i.e., filled with a fluid discussed above. The guide wire may be removed from the rest of the balloon assembly 1500 in order to allow other instruments (not shown) to access the hip joint 1595.

Figure 16:
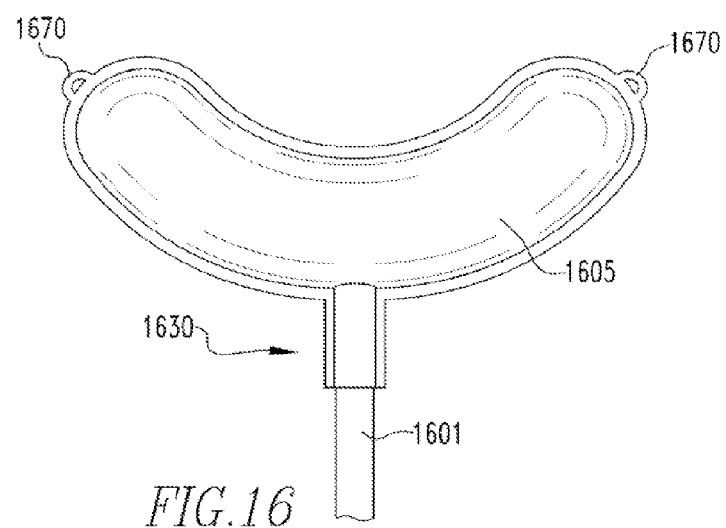
FIG. 16 is a top view of a balloon of a balloon assembly having suture tabs according to embodiments disclosed herein.

Referring to FIG. 16, a top view of a balloon 1605 of a balloon assembly having suture tabs 1670 in accordance with embodiments disclosed herein is shown. As shown, the balloon 1605 may be secured to a region near a distal end 1630 of a tubular member 1601. As discussed above, the balloon 1605 can be made of medical grade plastic. Further, the balloon can include radio opaque material. As shown, the balloon is in an inflated state and may include suture tabs 1670. The suture tabs 1670 may include openings through which a suture (not shown) may be threaded through at least one of the suture tabs 1670. By having suture threaded through at least one of the suture tabs 1670, a user may be able to steer, e.g., manipulate the balloon 1605 within a patient's body by pulling on the suture. For example, in one or more embodiments, a suture may be threaded through each of the suture tabs 1670 and a user may be able to pull on each of, or both of, the sutures to pull and manipulate the balloon 1605. Those having ordinary skill in the art will appreciate that the suture tabs 1670 may be any structure or feature of the balloon 1605 that may allow a suture to be threaded through a region of the balloon 1605. Further, those having ordinary skill in the art will appreciate that the balloon 1605 may include one, two, three, or more suture tabs 1670 that may be formed on any region of the balloon 1605.

Figure 17:
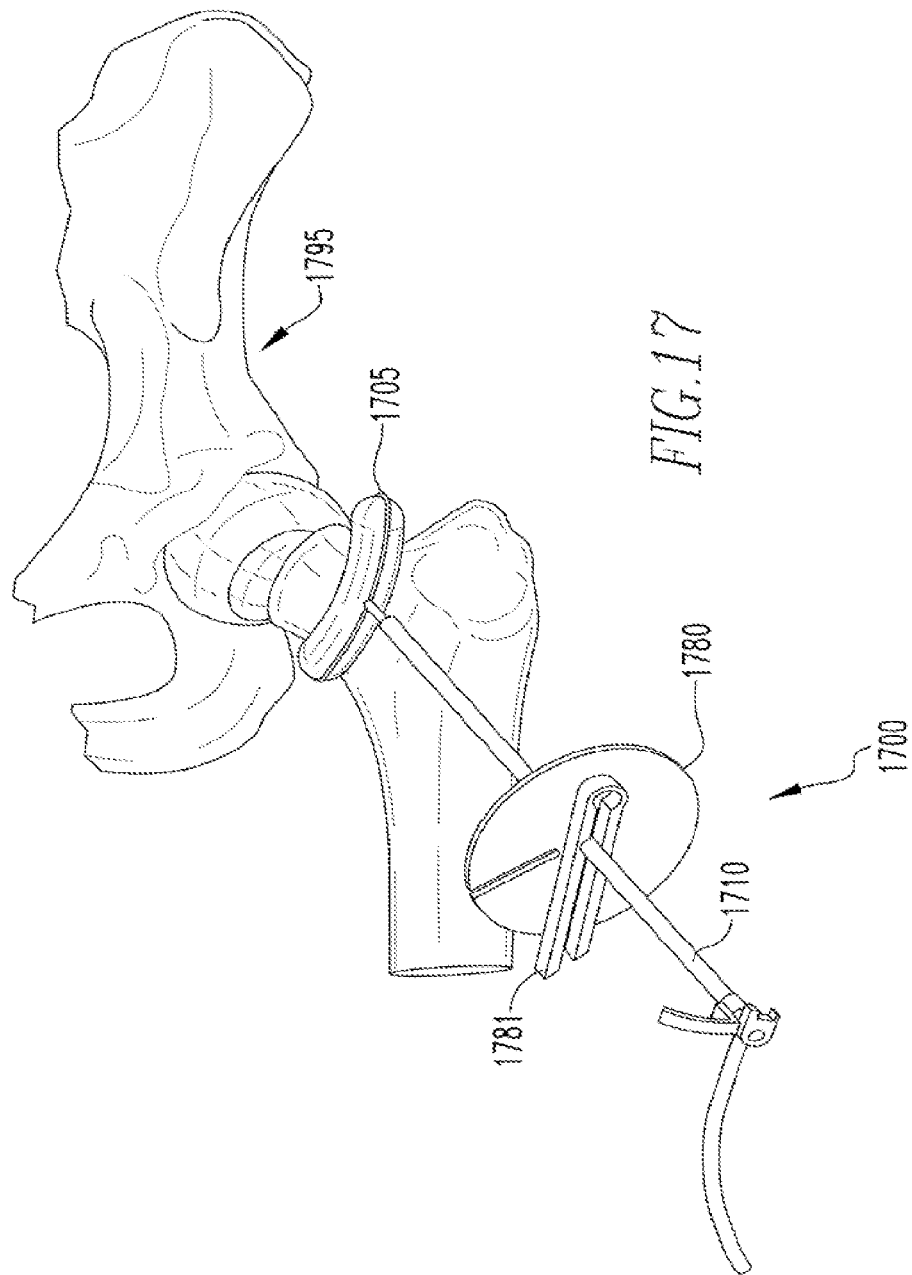
FIG. 17 is a perspective view of a balloon assembly in an inflated position with a skin pad and a clamp, in which a guide wire is disengaged and removed from the balloon assembly according to embodiments disclosed herein.

Referring to FIG. 17, a perspective view of a balloon assembly 1700 in an inflated position in a hip joint 1795 with a skin pad 1780 and a clamp 1781, in which a guide wire (not shown) is disengaged and removed from the balloon assembly 1700 in accordance with embodiments disclosed herein is shown. As shown, a sheath 1710 is positioned to expose a balloon 1705, and the balloon 1705 is inflated, i.e., filled with a fluid discussed above.

In one or more embodiments, the guide wire may be removed from the rest of the balloon assembly 1700 in order to allow other instruments (not shown) to access the hip joint 1795. Further, as shown, the skin pad 1780 and the clamp 1781 may be engaged with the sheath 1710 to secure the balloon assembly 1700 within the hip joint 1795. For example, the skin pad 1780 may be disposed around the sheath 1710 and disposed between clamp 1781 and an outer tissue or skin layer (not shown) of a body. In one or more embodiments, the skin pad 1780 may be made of any material known in the art and may serve as a buffer or intermediary to prevent any irritation or discomfort that may be caused by direct contact between the clamp 1781 and the outer tissue or skin layer.

In one or more embodiments, the sheath 1710 may not be required, and the skin pad 1780 and the clamp 1781 may be engaged with the tubular member 1701 instead of the sheath 1710 to secure the balloon assembly 1700 within the hip joint 1795. Those having ordinary skill in the art will appreciate that the clamp 1781 may be any fixation device or mechanism that may secure the balloon assembly 1700 within the hip joint 1795. For example, the clamp 1781 may be a removable pin, lock, adhesive, or sealant that may secure the balloon assembly 1700 within the hip joint 1795. By securing the balloon assembly 1700 within the hip joint 1795, the clamp 1781 may be able to maintain any pressure or tension between the balloon assembly 1700 and the hip joint 1795.

Figure 18:
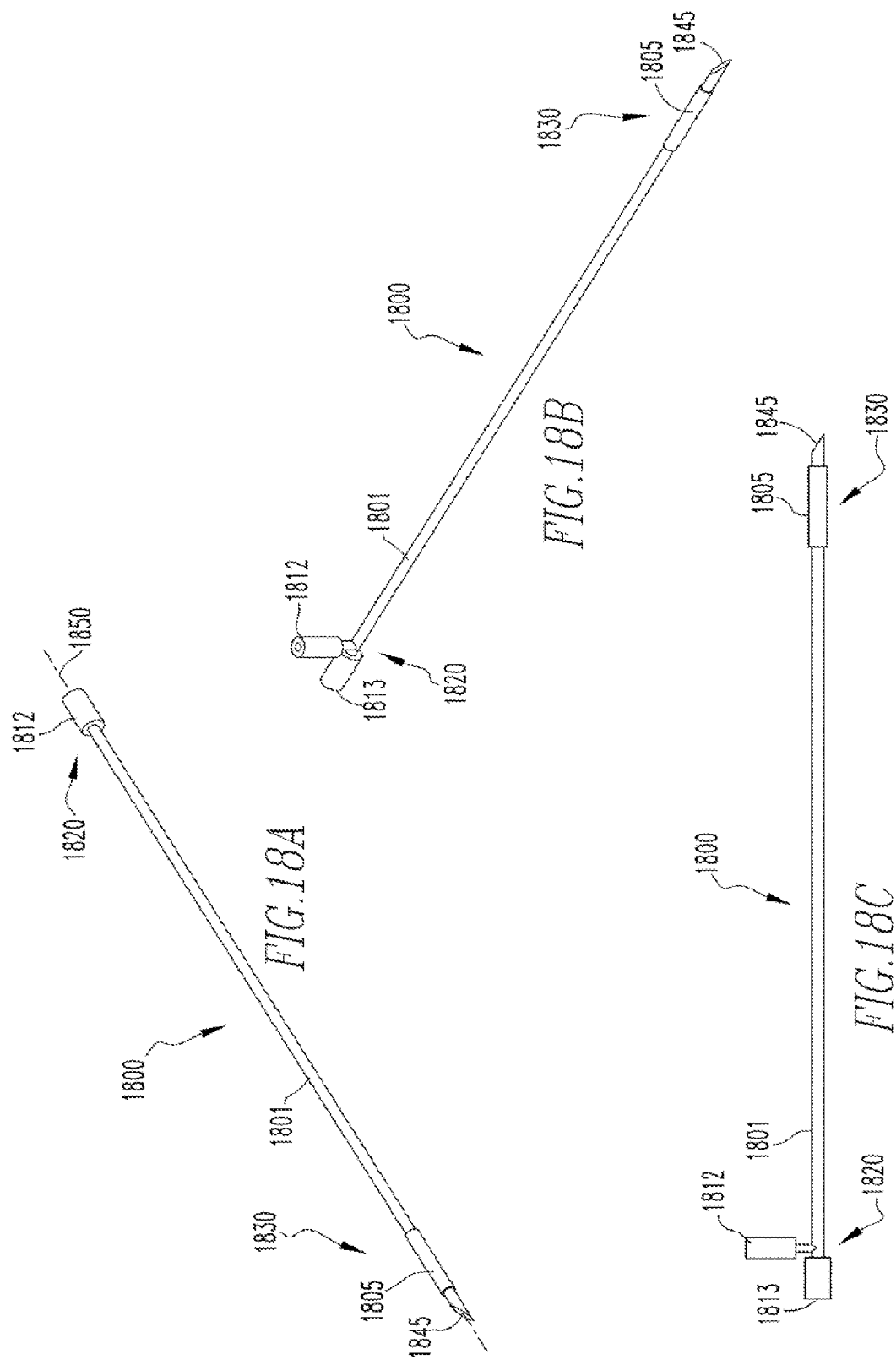
FIGS. 18A-18C are multiple views of a dilator assembly in a deflated state according to embodiments disclosed herein.

Referring, generally, to FIGS. 18A-18C, a dilator assembly 1800 in a deflated state in accordance with embodiments disclosed herein is shown. The dilator assembly 1800 is an apparatus for dilating tissue within a body and includes a tubular member 1801. As shown, the tubular member 1801 has a proximal end 1820, a distal end 1830, and a central axis 1850 defined therethrough. The tubular member 1801 may be made of stainless steel, ceramic, plastic or any material known in the art that may be substantially rigid. Although the tubular member 1801 shown in FIGS. 18A-18C is round, those having ordinary skill in the art will appreciate that the tubular member may be one of a variety of shapes and forms. For example, the tubular member may be square, triangular, hexagonal, or any other shape known in the art.

Further, the distal end 1830 of the tubular member 1801 may include a pointed tip 1845 configured to pierce a tissue (not shown) within a body (not shown). The pointed tip 1845, as shown, may be angled from 1 degree to 89 degrees from the axis 1850. Those having ordinary skill in the art will appreciate that the pointed tip 1845 may be configured with additional structures capable of piercing a tissue within a body. For example, the pointed tip may be arrow-shaped, needle-shaped, or may be any shape known in the art that may allow the pointed tip to pierce a tissue within a body.

Still referring to FIGS. 18A-18C, a balloon 1805 may be secured to a first region of the tubular member 1801. As shown, the balloon 1805 is secured to a region near the distal end 1830 of the tubular member 1801. The balloon 1805 may be secured to the tubular member 1801 by an adhesive or sealant known in the art. The balloon 1805 can be made of medical grade plastic. In some embodiments, the balloon can be made of biodegradable material such as without limitation, polylactic acid materials, glycolides, and other materials that may polymerize and degrade with time in the body. Such materials can include biodegradable polymers including, but not limited to, glycolic acid-based polymers, such as polyglycolide (PGA); lactic acid-based polymers, such as polylactide (PLA); polyanhydrides; polyorthoesters; polyphosphazenes; poly(dioxanone) copolymers; poly(trimethylene carbonate) copolymers; poly(e-caprolactone) homopolymers and copolymers; LPLA; DLPLA; PCL; PDO; PGA-TMC; DLPLG; and polyhydroxybutyrate (PHB) and polyhydroxyvalerate (PHV) polymers and copolymers, such as Biopol(r) (Monsanto Co., St. Louis, Mo.). In other embodiments, the balloon 1805 can be made of non-biodegradable material, for example, if the material is to remain intact for an extended period of time. The filling agent of the balloon 1805 can be any medically safe material including fluids such as liquid saline, dextrose solutions, water, gases, such as air or nitrogen, and other fluids. Further, the fluid can be a hardenable material, known to those in the art. The balloon 1805 can be provided in different sizes and shapes depending on the size of the tissue to be elevated. As shown, the balloon 1805 is substantially tube-shaped and is configured to dilate a tissue within a body.

Further, an outer surface of the balloon 1805 may be textured to provide increased friction between the balloon 1805 and the area in contact with the balloon 1805. Furthermore, the balloon 1805 may become substantially rigid upon inflation, which may provide a reinforced support within a patient's body. Moreover, the term "balloon" is used broadly to encompass one or more balloons. For example, multiple balloons can be placed in position instead of one larger balloon as may be appropriate for the particular growth to be removed. Further, the balloon can include radio opaque material. As shown, the balloon is in a deflated state.

As will be discussed below, in one or more embodiments, the tubular member 1801 may include, at least, a first lumen (not shown) and a second lumen (not shown) separately formed therein. Although the tubular member 1801 may have a first lumen and a second lumen, those having ordinary skill in the art will appreciate that the tubular member may include more or less lumens formed therein than described above. For example, the tubular member may have one, three, four, or more lumens formed therein. Further, as will be discussed below, in one or more embodiments, the proximal end 1820 of the tubular member 1801 may include, at least, an inflation port 1812 and a guide wire port 1813.

In one or more embodiments, the inflation port 1812 may be engagable with an injection mechanism (not shown). The injection mechanism may be one of a syringe, a pump, and a plunger. However, those having ordinary skill in the art will appreciate that the injection mechanism may be any device or mechanism capable of injecting a fluid, i.e., a liquid or gas, known in the art. In one or more embodiments, the injection mechanism may inject a fluid, e.g., a liquid or gas described above, through the inflation port 1812, into the first lumen (not shown) formed through the tubular member 1801, and into the balloon 1805 to inflate the balloon 1805 (shown and discussed below in FIGS. 19A-19D).

In one or more embodiments, the injection mechanism may also withdraw the fluid described above from the balloon 1805, causing the balloon 1805 to deflate. For example, this can be achieved by causing the injection mechanism to create a pull vacuum to withdraw the fluid from the balloon 1805, back through the first lumen and the tubular member 1801, and back into the injection mechanism.

In one or more embodiments, the injection mechanism may also include a pressure gauge (not shown) to monitor the pressure of the fluid that may be injected into the balloon 1805. Further, in one or more embodiments, the injection mechanism and/or the tubular member 1801 may include a seal (not shown). Once sealed, the seal may prevent a fluid, as described above, from withdrawing from the balloon 1805, the first lumen, and/or the tubular member 1801 back into the injection mechanism. The seal may be self-sealing, such as a check valve, a dome valve, and a self-sealing septum. The check valve can include valves such as read valves, flapper valves, and other self-sealing valves know in the art. In at least one embodiment, the seal can seal against the first lumen within the tubular member 1801. Further, the inflation port 1812 may include a lock (not shown) to secure the injection mechanism to the inflation port 1812.

Referring still to FIGS. 18A-18C, the guide wire port 1813 may be engagable with a guide wire (not shown). In one or more embodiments, the guide wire may be substantially disposed within the guide wire port 1813 and substantially disposed within the second lumen (not shown) of the tubular member 1801. The guide wire may be a device or mechanism that may be controllably manipulated, deformed, or deflected. For example and without limitation, another exemplary guide wire device is shown in U.S. Pat. No. 6,283,960. The teaching of the above disclosure is incorporated herein by reference in its entirety.

In one or more embodiments, the guide wire can provide guidance for various tools, balloons, and other instruments inserted into a body. Further, variations on the use of the guide wire, including a guide wire external to balloon or internal to the balloon, no guide wire, guide wire at different steps, retracting the guide wire at different steps, and other variations are possible. The guide wire port 1813 may include a lock (not shown) to secure a portion of the guide wire to the guide wire port 1813.

Referring to FIGS. 18A-18D, although the proximal end 1820 of the tubular member 1801 is shown to include an injection port 1812 and a guide wire port 1813, those having ordinary skill in the art will appreciate that, in an alternative embodiment, a Y-adaptor (not shown), as discussed above and shown in FIGS. 1A-1D, may be secured at a region at or near the proximal end 1820 of the tubular member 1801 of the dilator assembly 1800. The Y-adaptor may also include a lock (not shown) on the inflation port 1812 to secure the injection mechanism to the inflation port 1812. Further, the Y-adaptor may also include a lock (not shown) on the guide wire port 1813 to secure a portion of the guide wire to the guide wire port 1813.

Referring, generally, to FIGS. 19A-19D, a dilator assembly 1900 in an inflated state in accordance with embodiments disclosed herein is shown. The dilator assembly 1900 is an apparatus for dilating tissue within a body and includes a tubular member 1901 and a balloon 1905. As shown, the tubular member 1901 has a proximal end 1920, a distal end 1930, and a central axis 1950 defined therethrough.

As discussed above regarding the dilator assembly 1800, the distal end 1930 may include a pointed tip 1945 configured to pierce a tissue (not shown) within a body (not shown). The pointed tip 1945, as shown, may be angled from 1 degree to 89 degrees from the axis 1950. Those having ordinary skill in the art will appreciate that the pointed tip 1945 may be configured with additional structures capable of piercing a tissue within a body. For example, the pointed tip may be arrow-shaped, needle-shaped, or may be any shape known in the art that may allow the pointed tip to pierce a tissue within a body. The balloon 1905 is configured to dilate a tissue within a body and may be substantially similar to the balloon 1805, as discussed above. As shown, the balloon 1905 is in an inflated state.

In one or more embodiments, the tubular member 901 may include, at least, a first lumen 1922 and a second lumen 1923 separately formed therein. As discussed above, the proximal end 1920 of the tubular member 1901 may include, at least, an inflation port 1912 and a guide wire port 1913. The inflation port 1912 may be engagable with an injection mechanism (not shown), as discussed above. In one or more embodiments, the injection mechanism may inject a fluid, e.g., a liquid or gas described above, through the inflation port 1912, into the first lumen 1922 formed through the tubular member 1901, and into the balloon 1905 to inflate the balloon 1905. In one or more embodiments, the injection mechanism may also withdraw the fluid described above from the balloon 1905, causing the balloon 1905 to deflate. For example, this can be achieved by causing the injection mechanism to create a pull vacuum to withdraw the fluid from the balloon 1905, back through the first lumen 1922 and the tubular member 1901, and back into the injection mechanism. Further, in one or more embodiments, the injection mechanism and/or the tubular member 1901 may include a seal (not shown) and a pressure gauge (not shown), as discussed above.

Referring still to FIGS. 19A-19D, the guide wire port 1913 may be engagable with a guide wire (not shown), as discussed above. In one or more embodiments, the guide wire may be substantially disposed within the guide wire port 1913 and substantially disposed within the second lumen 1923 of the tubular member 1901.

Figure 19:
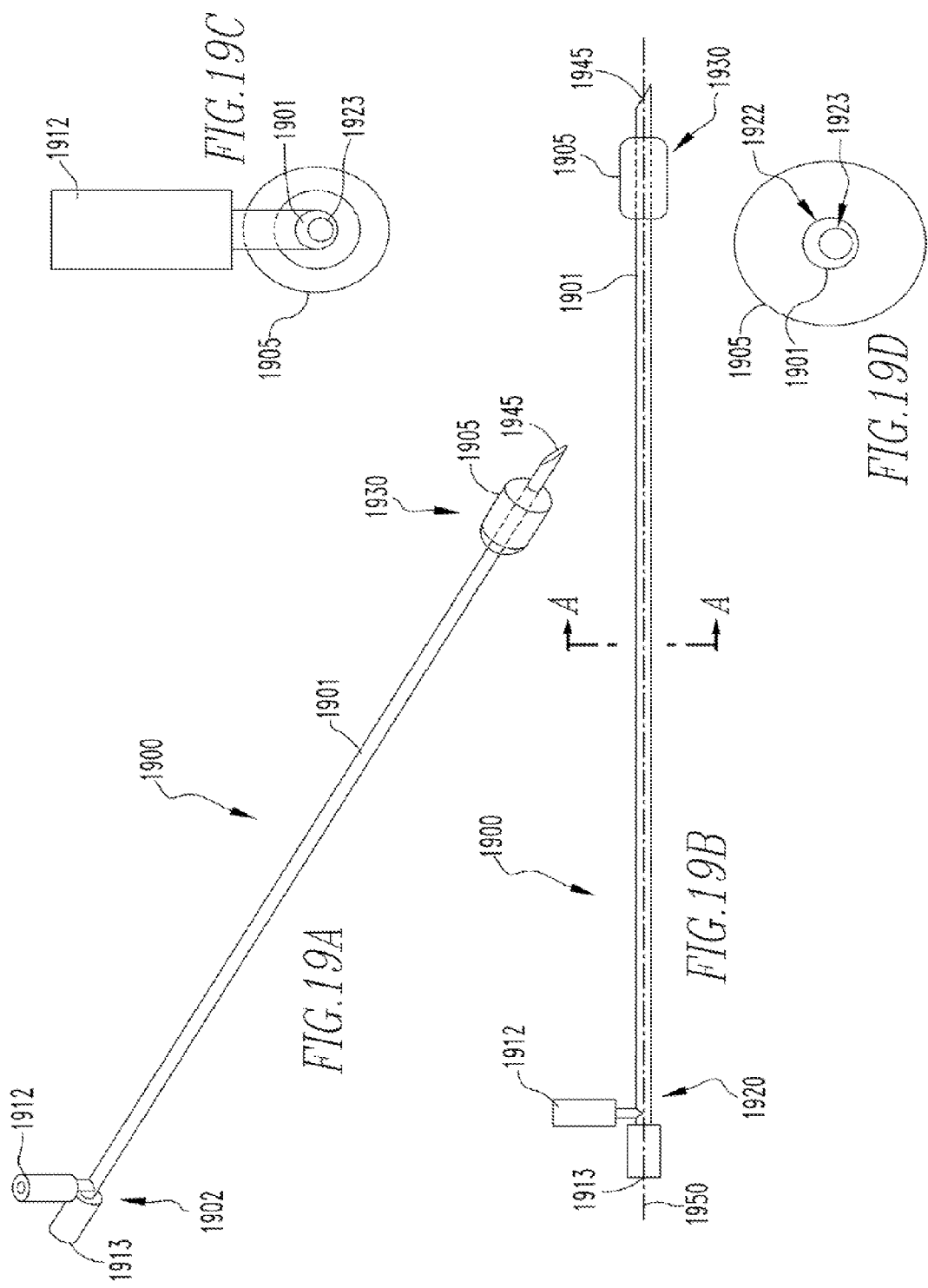
FIGS. 19A-19D are multiple views of a dilator assembly in an inflated state according to embodiments disclosed herein.

Referring now to FIGS. 19A and 19C, a schematic drawing of the dilator assembly 1900 and a front view of the dilator assembly 1900 according to embodiments disclosed herein are shown, respectively. As shown, a second lumen 1923 may extend completely through the tubular member 1901 and allow a guide wire (not shown) to be engaged with the tubular member 1901 and may allow the guide wire to enter the tubular member 1901 through the guide wire port 1913 at the proximal end 1920 of the tubular member through the second lumen 1923 and exit the tubular member 1901 at the distal end 1930 of the tubular member 1901 through the second lumen 1923 and into a body (not shown). Further, those having ordinary skill in the art will appreciate that embodiments of the present invention are not limited to only allowing a guide wire to be engaged with the tubular member 1901 and received within the second lumen 1923 of the tubular member 1901. For example, the second lumen of the tubular member may be configured to receive a balloon assembly, as described above, a trocar, or any other surgical device known in the art.

Referring to FIGS. 19A and 19D, a schematic drawing of the dilator assembly 1900 and a cross-sectional view of the tubular member 1901 of the dilator assembly 1900 in accordance with embodiments disclosed herein are shown, respectively. As shown, the tubular member 1901 includes the first lumen 1922 and the second lumen 1923 separately formed therethrough. Further, as shown, a cross-section of the first lumen 1922 is substantially a crescent shape and a cross-section of the second lumen 1923 is substantially circular in shape. Those having ordinary skill in the art will appreciate that the cross-sections of the first lumen 1922 and the second lumen 1923 are not limited to the shapes described above. For example, the cross-section of the first lumen may be any shape that may allow a fluid, e.g., a liquid or a gas described above, to move or travel through the first lumen. Further, the cross-section of the second lumen may be any shape that may allow a guide wire, as described above, a balloon assembly, as described above, or other surgical device known in the art to be disposed within the second lumen. For example, the cross-section of the second lumen may be any shape to substantially fit an outer diameter of the guide wire, a balloon assembly, or another surgical device known in the art.

A method of elevating tissue within a body, in accordance with embodiments disclosed herein, may include providing a tubular member having a proximal end and a distal end and a central axis defined therethrough, inserting the distal end of the tubular member into a joint, and inflating a balloon within the joint, causing a tissue to elevate relative to a position of the tissue prior to inserting the balloon into the joint. The balloon may be secured to a region of the tubular member and an injection mechanism may be configured to inflate the balloon. A guide wire may be configured to engage with the tubular member and the guide wire may be configured to manipulate the tubular member.

The method may also include manipulating the tubular member within the joint. Inflating the balloon, as described above, may include injecting a fluid, e.g., a liquid or gas describe above, into the balloon. The method may also include providing a sheath disposed around the balloon and removing the sheath once the balloon is disposed, at least partially, within the joint. Further, inflating the balloon may cause a capsule tissue to elevate from a femoral neck relative to a position of the capsule tissue prior to inserting the balloon into the joint. Furthermore, the balloon, as described above, may become substantially rigid upon inflating the balloon within the joint. The method may also include deflating the balloon within the joint and removing the tubular member from within the joint. The method may also include a sheath lock that is engaged with the tubular member, disengaging the sheath lock from the tubular member, and moving the sheath along the tubular member in a direction that is parallel with the axis of the tubular member, in which the balloon is exposed from the sheath. Further, the method may include a sheath having a sheath trigger, moving the sheath trigger such that the sheath moves along the tubular member in a direction that is parallel with the axis of the tubular member, in which the balloon is exposed from the sheath. The method may also include a guide wire having a handle, in which the handle includes an engagement latch, in which the engagement latch of the guide wire is configured to engage with an engagement member of the tubular member. The method may also include disengaging the engagement latch of the handle of the guide wire from the engagement member of the tubular member and disengaging the guide wire from the tubular member, in which disengaging the guide wire from the tubular member includes removing, e.g., withdrawing, the guide wire from within the tubular member. Finally, the method may include disposing a skin pad between near an outer tissue surface of a body and securing a clamp against the skin pad.

A kit for elevating tissue within a body, in accordance with embodiments disclosed herein, may include a tubular member having a proximal end and a distal end, a balloon configured to engage with the tubular member, an injection mechanism configured to engage with the tubular member, and a guide wire configured to engage with the tubular member. The injection mechanism may be configured to inflate the balloon and the guide wire may be configured to manipulate the tubular member. Further, the balloon may be substantially kidney shaped and may be configured to engage a femoral neck and elevate a tissue within a joint. Finally, an outer surface of the balloon may be a textured surface.

A method of dilating tissue within a body in accordance with embodiments disclosed herein, may include providing a tubular member having a proximal end and a distal end and a central axis defined therethrough, inserting the distal end of the tubular member into a joint, and inflating the balloon within the joint, causing a tissue to dilate relative to a position of the tissue prior to inserting the balloon into the joint. The balloon may be secured to a first region of the tubular member, the balloon may be disposed, at least partially, within a joint, and an injection mechanism may be configured to inflate the balloon. The distal end of the tubular member comprises a pointed tip configured to pierce a tissue within a body.

The method may also include inserting the guide wire into the tubular member and into the joint, in which the guide wire is configured to engage with the tubular member. Inflating the balloon, as described above, may include injecting a fluid, e.g., a liquid or a gas described above, into the balloon within the joint. Further, inflating the balloon may cause a capsule tissue to dilate relative to a position of the capsule tissue prior to inserting the balloon into the joint. Furthermore, as described above, the balloon may become substantially rigid upon inflating the balloon. The method may also include deflating the balloon within the joint, in which deflating the balloon comprises removing a fluid from within the balloon. The method may also include removing the tubular member from the joint, in which the guide wire remains in the joint.

A kit for dilating tissue within a body, in accordance with embodiments disclosed herein, may include a tubular member having a proximal end and a distal end, a balloon configured to engage the tubular member, an injection mechanism configured to engage with the tubular member, and a guide wire configured to engage with the tubular member. The distal end of the tubular member may include a pointed tip configured to pierce a tissue within a body. The injection mechanism may be configured to inflate the balloon. Further, the balloon may be configured to dilate a tissue within a joint and may become substantially rigid upon inflating the balloon within a joint. Finally, an outer surface of the balloon may be a textured surface.

Figure 20:
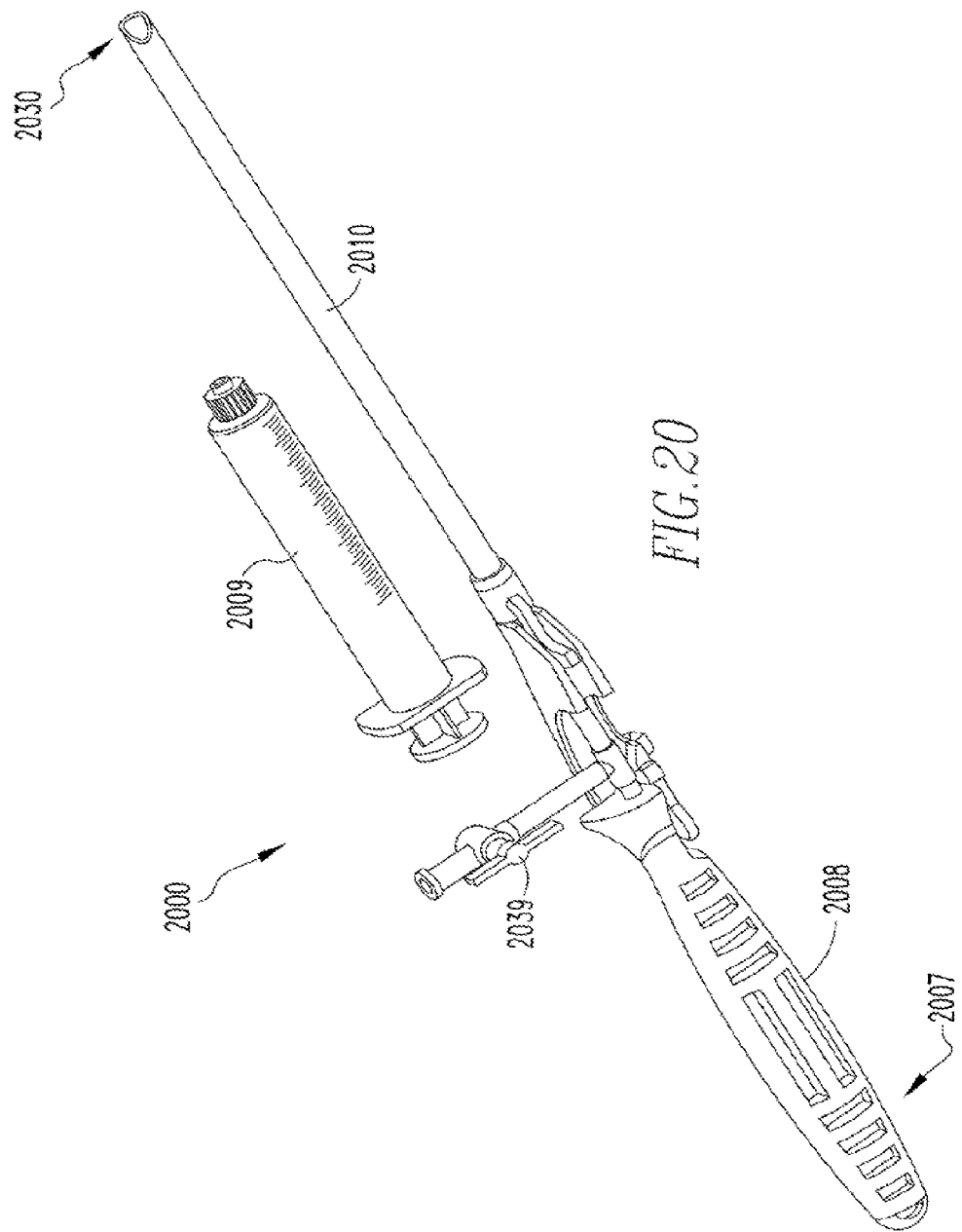
FIG. 20 is a perspective view of a balloon assembly with a sheath according to embodiments disclosed herein.

Referring to FIG. 20, a balloon assembly 2000 with a sheath 2010 in accordance with embodiments disclosed herein is shown. The balloon assembly 2000 is an apparatus for elevating tissue within a body and includes a tubular member (not shown) and a central axis formed therethrough. As shown, the balloon assembly 2000 has a sheath 2010 disposed around the tubular member and around a deflated balloon (not shown) that may be secured to a distal end of the tubular member. As the sheath 2010 may be disposed around the tubular member and the deflated balloon, the sheath 2010 may assist in the delivery of the balloon assembly 2000 into a body (not shown).

In one or more embodiments, a distal end 2030 of the sheath 2010 may be a beveled, or angled, end to assist in the delivery of the balloon assembly 2000 into the body. For example, as shown, the distal end 2030 of the sheath 2010 may be angled to assist with the delivery of the delivery of the sheath 2010, the tubular member, and the balloon into a tissue within a body. In one or more embodiments, the distal end 2030 of the sheath 2010 may be cut to a 45 degree angle. However, those having ordinary skill in the art will appreciate that the distal end 2030 of the sheath 2010 may be angled to angles greater than or less than 45 degrees, including any angle between 1 degree and 89 degrees from a central axis of the tubular member or from a central axis of the sheath 2010. For example, in one or more embodiments, the distal end 2030 of the sheath 2010 may be cut to a 15 degree angle. Alternatively, in one or more embodiments, the distal end 2030 of the sheath 2010 may be cut to a 75 degree angle. Further, as shown, in one or more embodiments, the distal end 2030 of the sheath 2010 may have a flat tip, such that the distal end 2030 of the sheath 2010 may assist with delivery of the sheath 2010 into a tissue within a body, but may not necessarily pierce the tissue.

As discussed above, the balloon assembly 2000 may include a guide wire 2007 that may be received within the tubular member such that the guide wire may manipulate, deform, or deflect the tubular member. As shown, the guide wire 2007 may include a handle 2008. The handle 2008 of the guide wire 2007 may provide a user with a gripping area to hold and operate the guide wire 2007.

Further, as shown, the balloon assembly 2000 may include an injection mechanism 2009. As shown, the injection mechanism 2009 may include a stop valve 2039 and may be connected to the tubular member by a tubing (not shown). Those having ordinary skill in the art will appreciate that the tubing may be flexible or rigid, and may be made of any known material in the art. For example, the tubing may be a flexible, rubber or plastic tubing. Alternatively, the tubing may be made of a rigid plastic or other rigid material known in the art.

As discussed above, the injection mechanism 2009 may be one of a syringe, a pump, a plunger, or any device or mechanism capable of injecting a fluid, i.e., a liquid or a gas, known in the art. In one or more embodiments, a fluid, e.g. a liquid or a gas described above, may be injected by the injection mechanism 2009 into the tubular member and into an interior of the balloon, inflating the balloon. The stop valve 2039 may be used to prevent backflow of fluid back into the injection mechanism 2009 and may be used to assist in maintaining fluid pressure within the balloon. Those having ordinary skill in the art will appreciate that the stop valve 2039 may be any valve, device, or mechanism that is capable of preventing fluid flow in a given direction.

Figure 21:
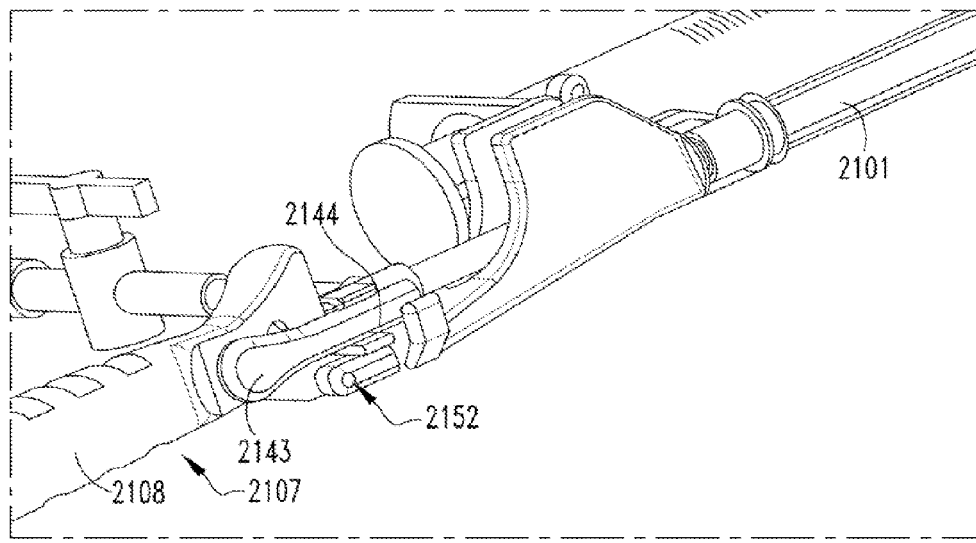
FIG. 21 is a close-up view of an engagement latch of a handle of a guide wire in an engaged position according to embodiments disclosed herein.

Referring to FIG. 21, a perspective view of an engagement latch 2152 of a handle 2108 of a guide wire 2107 in an engaged position in accordance with embodiments disclosed herein are shown. As shown, the engagement latch 2152 may be coupled to the handle 2108 of the guide wire 2107 and may include a first end 2143, a second end 2144, and a detent (not shown) extending from a region near the second end 2144 of the engagement latch 2152.

In one or more embodiments, the detent of the engagement latch 2152 may prevent the handle 2108 of the guide wire 2107 from moving away from the tubular member 2101 in a direction that is parallel to a central axis. In other words, the detent of the engagement latch 2152 may prevent the guide wire 2107 from being withdrawn from the tubular member 2101. In one or more embodiments, the engagement latch 2152 may be configured to engage with an engagement member (not shown) of a tubular member 2101. In one or more embodiments, the engagement member of the tubular member 2101 may be disposed on a region near a proximal end of the tubular member 2101.

As shown, the engagement latch 2152 of the handle 2108 of the guide wire 2107 is engaged with the engagement member of the tubular member. In one or more embodiments, the engagement latch 2152 of the handle 2108 of the guide wire 2107 may be a see-saw-type mechanism, such that moving the first end 2143 of the engagement latch 2152 in a first direction may cause the second end 2144 of the engagement latch 2152 to move in a second direction that is opposite to the first direction. For example, in one or more embodiments, by pressing on the first end 2143 of the engagement latch 2152, the second end 2144 of the engagement latch may disengage from the engagement member of the tubular member 2101. In one or more embodiments, the engagement latch 2152 and the detent of the engagement latch 2152 may no longer be in contact with the engagement member in the disengaged position. As such, in one or more embodiments, the guide wire 2107 may be withdrawn from the tubular member 2101 with the engagement latch 2152 in the disengaged position.

Figure 22:
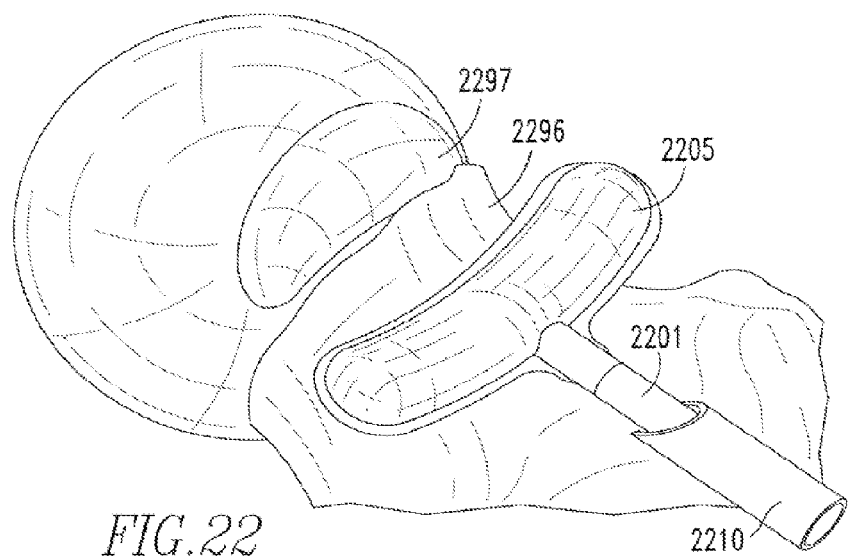
FIG. 22 is a perspective view of a balloon engaged with a femoral neck according to embodiments disclosed herein.

Referring to FIG. 22, a perspective view of a balloon 2205 engaged with a femoral neck 2296, in accordance with embodiments disclosed herein, is shown. As shown, the balloon 2205 is fully inflated and is engaged with the femoral neck 2296. In one or more embodiments, the balloon 2205 may be substantially crescent shaped. However, those having ordinary skill in the art will appreciate that the balloon 2205 may be formed in a variety of shapes that are configured to engage with the femoral neck 2296. For example, in one or more embodiments, the balloon 2205 may be substantially sausage-shaped, kidney-shaped, or bean-shaped. Further, although not shown, in one or more embodiments, the balloon 2205 may be reinforced with a fabric mesh, such as a nylon mesh. In one or more embodiments, fabric mesh reinforcement may allow the balloon 2205 to sustain higher pressures.

Furthermore, in one or more embodiments, the balloon 2205 material may be of a fluorescent, contrasting color, such as an orange color, in order to create contrast between the balloon 2205 and any bone, tissue, or area within the body. Those having ordinary skill in the art will appreciate that the balloon 2205 color may be any color that may contrast with any bone, tissue, or area within the body. For example, in one or more embodiments, the balloon 2205 may be blue, black, yellow, green, or any other color known in the art that may create some contrast between the balloon 2205 and any bone, tissue, or area within a body.

Alternatively, in one or more embodiments, the balloon 2205 material may be clear, or translucent, and may be filled with a colored fluid, or a fluid with a coloring agent, in order to create contrast between the balloon 2205 and any bone, tissue, or area within a body. For example, in one or more embodiments, the balloon 2205 material may be clear, or translucent, and may be filled with a colored fluid, or a fluid with a coloring agent, that is blue, black, yellow, green, or any other color known in the art that may contrast with any bone, tissue, or area within a body.

As shown, the balloon 2205 is coupled to a tubular member 2201, which may have a sheath 2210 disposed about the tubular member 2201. As shown, the sheath 2210 is in a retracted position, exposing the balloon 2205. As discussed above, the sheath 2210 may be used to assist with delivery of the balloon 2205 into a body. In one or more embodiments, once positioned inside the body, the balloon 2205 may be inflated (as shown) and may be used to manipulate, or dilate, tissue within the body. This manipulation, or dilation, of the tissue may allow other areas within the body in proximity of the femoral neck 2296 to be exposed. For example, in one or more embodiments, the inflated balloon 2205 may allow instrumental access to the region 2297. In one or more embodiments, the inflated balloon 2205 may allow an instrument, including any surgical instrument known in the art, to access the body in proximity of the femoral neck 2296 may allow procedures to be done on an area within the body, e.g., the region 2297. For example, in one or more embodiments, the region 2297 may be accessed with a surgical instrument and shaved down, or partially removed, from the body.

Although the aspects of the present invention discussed above may apply to surgical procedures involving joints, those having ordinary skill in the art will appreciate that these aspects of the present invention may apply to other areas of the body as well. For example, aspects of the present invention may also be applied to the knee joint, e.g., the tibia, femur, patella, and the surrounding tissues, tendons, muscles, and ligaments, such as the ACL, PCL, MCL, and the patellar tendon. For example, the patella tendon and the MCL may be lifted according to aspects of the current invention to gain access to the tibia/femur. Further, the shoulder, wrist, and ankle joints all contain various bones having surrounding tissues, tendons, muscles, and ligaments. Aspects of the present invention can be applied to tissues, muscles, tendons, and ligaments that exist in these joint areas that need to be lifted in order to gain working space, visualization, and access to particular areas of interest.

Advantageously, embodiments disclosed herein may provide a maneuverable balloon assembly that may be maneuvered inside of a body. Additionally, the balloon assembly, according to embodiments disclosed herein, may allow for expanding or separating tissues in order to create a space between the tissue to improve visualization and for increased working space during open surgery and minimally invasive surgery. The balloon assembly, according to embodiments disclosed herein, may also allow a surgeon to maneuver into small, tight, potential spaces within the body and turn them into existing spaces safely, easily, and controllably in order to safely visualize appropriate tissue and operate. Creating these types of spaces within the body may allow for selective retraction of tissue, either of hard tissue such as bone or soft tissue planes, to be moved out of the way to improve working space and visualization. As some joints and spaces in the body are smaller than others, the balloon assembly, according to embodiments disclosed herein, may provide the maneuverability necessary to access these areas and elevate and/or separate tissues and muscles within these areas, in a minimally invasive way.

While embodiments have been described with respect to a limited number of embodiments, those skilled in the art, having benefit of this disclosure, will appreciate that other embodiments can be devised which do not depart from the scope of embodiments disclosed herein. Accordingly, the scope of embodiments disclosed herein should be limited only by the attached claims.

What is claimed is:

1. A method of elevating tissue within a body, comprising:
    providing a tubular member having a proximal end and a distal end and a central axis defined therethrough, the tubular member comprising a first lumen and a second lumen, separately formed therein, the first lumen having a distal opening at its distal end, the distal end of the first lumen located at the distal end of the tubular member, the second lumen comprising a distal stop formed on a first region of the tubular member proximate the distal end,
    wherein a balloon having an interior and a single opening to the interior is secured to a second region of the tubular member, the second region of the tubular member at or near the distal end of the tubular member, the distal end of the tubular member located within the interior of the balloon, wherein an injection mechanism is engaged to a third region of the tubular member and configured to inflate the balloon, wherein the first lumen provides a path for communication between the injection mechanism and the interior of the balloon wherein a guide wire is configured to engage with the tubular member, wherein the guide wire is configured to manipulate the tubular member from within the second lumen;

inserting a guide wire into the second lumen from the proximal end to the distal stop;

inserting the distal end of the tubular member into a joint, wherein the balloon is disposed, at least partially, within the joint; and inflating the balloon within the joint, causing a tissue to elevate relative to a position of the tissue prior to inserting the balloon into the joint.

2. The method of claim 1, further comprising manipulating the tubular member within the joint.

3. The method of claim 1, wherein inflating the balloon within the joint comprises injecting a fluid into the balloon.

4. The method of claim 1, wherein inflating the balloon causes a capsule tissue to elevate from a femoral neck relative to a position of the capsule tissue prior to inserting the balloon into the joint.

5. The method of claim 1, further comprising deflating the balloon within the joint.

6. The method of claim 1, further comprising removing the tubular member from the joint.

7. The method of claim 1, further comprising providing a sheath disposed around the balloon and removing the sheath once the balloon is disposed, at least partially, within the joint.

8. The method of claim 7, further comprising moving the sheath along the tubular member in a direction that is parallel with the central axis of the tubular member, wherein the balloon is exposed from the sheath.

9. A method of elevating tissue within a body, comprising:
inserting a distal portion of a tubular member and a balloon secured to the distal portion of the tubular member into a joint;
inflating the balloon within the joint via a first lumen formed within the tubular member, the first lumen extending into the balloon; and
inserting a guide wire into a second lumen formed within the tubular member separately from the first lumen, the second lumen comprising a distal stop proximate a distal end of the tubular member, wherein the guide wire is inserted from a proximal end of the second lumen to the distal step.

10. The method of 9, further comprising manipulating the tubular member within the joint.

11. The method of 9, wherein inflating the balloon within the joint comprises injecting a fluid into the balloon.

12. The method of 9, wherein inflating the balloon causes a capsule tissue to elevate from a femoral neck relative to a position of the capsule tissue prior to inserting the balloon into the joint.

13. The method of 9, further comprising deflating the balloon within the joint.

14. The method of 9, further comprising removing the tubular member from the joint.

15. The method of 9, further comprising providing a sheath disposed around the balloon and removing the sheath once the balloon is disposed, at least partially, within the joint.

16. The method of 15, further comprising moving the sheath along the tubular member in a direction that is parallel with the central axis of the tubular member, wherein the balloon is exposed from the sheath.

* * * * *